(12) United States Patent
Bovin et al.

(10) Patent No.: US 9,821,080 B2
(45) Date of Patent: Nov. 21, 2017

(54) IN VIVO METHODS OF MONITORING BIODISTRIBUTION

(76) Inventors: Nikolai Vladimirovich Bovin, Moscow (RU); Stephen Henry, Auckland (NZ); Elena Yurievna Korchagina, Moscow (RU); Igor Leonidovich Rodionov, Puschino (RU); Alexander Borisovich Tuzikov, Moscow (RU)

( * ) Notice: Subject to any disclaimer, the term of this patent is extended or adjusted under 35 U.S.C. 154(b) by 792 days.

(21) Appl. No.: 13/984,050

(22) PCT Filed: Feb. 9, 2012

(86) PCT No.: PCT/NZ2012/000012
§ 371 (c)(1),
(2), (4) Date: Oct. 16, 2013

(87) PCT Pub. No.: WO2012/121610
PCT Pub. Date: Sep. 13, 2012

(65) Prior Publication Data
US 2014/0161723 A1    Jun. 12, 2014

(30) Foreign Application Priority Data
Feb. 9, 2011   (NZ) ........................................ 591047

(51) Int. Cl.
*A61K 51/08* (2006.01)
*C07F 9/10* (2006.01)
*A61K 51/04* (2006.01)

(52) U.S. Cl.
CPC .......... *A61K 51/08* (2013.01); *A61K 51/0408* (2013.01); *A61K 51/088* (2013.01); *C07F 9/10* (2013.01)

(58) Field of Classification Search
None
See application file for complete search history.

(56) References Cited

U.S. PATENT DOCUMENTS

| 4,571,332 | A | 2/1986 | Schroit et al. | |
| 4,623,485 | A | 11/1986 | Kono et al. | |
| 2008/0206130 | A1* | 8/2008 | Hallahan | A61K 41/0038 424/1.11 |

FOREIGN PATENT DOCUMENTS

| EP | 0 094 251 | 11/1983 |
| EP | 0 588 754 | 3/1994 |
| WO | WO 2008/030115 A2 | 3/2008 |
| WO | WO 2009/048343 A1 | 4/2009 |

OTHER PUBLICATIONS

Winzelberg et al. Detection of gastrointestinal bleeding with 99mTc-labeled red blood cells. 1982 Semin. Nucl. Med. 12: 139-146.*
Blake et al. Fluorophore-kodecytes—fluorescent function-spacer-lipid (FSL) modified cells for in vitro and in vivo analyses. 2010 FEBS J. 227(S1): 199.*
Sakahara et al. Avidin-biotin system for delivery of diagnostic agents. 1999 Adv. Drug Deliv. Rev. 37: 89-101.*
Hadac, E.M., et al; "Fluorescein and radiolabeled Function-Spacer-Lipid constructs allow for simple in vitro and in vivo bioimaging of envelope virions", *Journal of Virological Methods;* vol. 176, pp. 78-84 (2011).
Supplementary European Search Report dated Apr. 7, 2016 issued in EP 12755058, 4 pages.
T.J. Tsomides et al, "Stoichiometric Labeling of Peptides by Iodination on Tyrosyl or Histidyl Residues" *Analytical Biochemistry,* vol. 210, No. 1, Apr. 1, 1993, pp. 129-135.
M. Yamamoto et al, "Current Issues and Future Directions of Oncolytic Adenoviruses" *Molecular Therapy,* vol. 18, No. 2, Nov. 24, 2009, pp. 243-250.

* cited by examiner

*Primary Examiner* — Michael G. Hartley
*Assistant Examiner* — Jennifer Lamberski
(74) *Attorney, Agent, or Firm* — Nixon & Vanderhye P.C.

(57) ABSTRACT

Non-invasive method of monitoring by radioactivity bioscanning the distribution of a biological entity in a subject in vivo by administering to the subject a radioiodinated form of the biological entity. The radioiodinated form is prepared by contacting an aqueous suspension of the biological entity with a radioiodinated construct of the structure F-S-L where F comprises a radioiodinated tyrosine moiety, S is a spacer covalently linking F to L, and L is a lipid.

8 Claims, 13 Drawing Sheets
(3 of 13 Drawing Sheet(s) Filed in Color)

FIGURE 6

IN VIVO METHODS OF MONITORING BIODISTRIBUTION

This application is the U.S. national phase of International Application No. PCT/NZ2012/000012 filed 9 Feb. 2012 which designated the U.S. and claims priority to New Zealand Patent Application No. 591047 filed 9 Feb. 2011, the entire contents of each of which are hereby incorporated by reference.

FIELD OF INVENTION

The invention relates to a non-invasive method of monitoring the distribution of cells and virions in vivo and constructs for use in the method.

BACKGROUND ART

Existing methods for monitoring the distribution of biological entities in vivo require covalent or genetic modification of the entity. Such modification may result in the behaviour of the biological entity in vivo being modified.

Therapeutic applications where viruses are administered to a subject are in development. These applications include gene therapy and tumour destruction (oncolytic virotherapy) (Lui et al (2007)). In the development of these therapies it is a requirement to be able to monitor the distribution of the virion following administration without altering its infectivity (Herschman (2003); Yamamoto and Curiel (2010))

Monitoring the distribution of virions following administration is problematic employing existing methods. Tissue biopsy is invasive and is of limited use in clinical trials (Kuruppu and Tanabe (2005); Waehler et al (2007)). Non-invasive methods such as magnetic resonance imaging (MRI), positron emission tomography (PET) and X-ray computed tomography (CT) usually require image enhancing agents or chemical modification of the virion (Piwnica-Worms et al (2004); Strable and Finn (2009)).

Viruses may be engineered to incorporate reporter genes. However, monitoring the expression of these genes only indicates where the genes of the virus are being expressed (Peng et al (2003); Waehler et al (2007)).

It is an object of this invention to provide a convenient alternative to these existing methods with application to biological entities in addition to enveloped viruses (virions).

STATEMENT OF INVENTION

In a first aspect the invention provides a method of radiolabelling a biological entity comprising the step of contacting a suspension of the biological entity with an iodinated ($^{125}$I) construct of the structure F-S-L for a time and at a temperature sufficient to allow localisation of the $^{125}$I to the surface of the biological entity where F comprises an iodinated histidine (His) residue or an iodinated tyrosine (Tyr) residue, S is a spacer covalently linking F to L, and L is a lipid.

In a second aspect the invention provides a non-invasive method of monitoring the distribution of a biological entity in a subject in vivo comprising the steps of:
 contacting a suspension of the biological entity with a an iodinated ($^{125}$I) construct of the structure F-S-L for a time and at a temperature sufficient to provide a $^{125}$I-labelled biological entity;
 administering to the subject the $^{125}$I-labelled biological entity to a subject; and
 monitoring the distribution of the biological entity by radioactivity bioscanning,
where F comprises an iodinated histidine (His) residue or an iodinated tyrosine (Tyr) residue, S is a spacer covalently linking F to L, and L is a lipid.

Preferably, the suspension is an aqueous suspension. S is selected to provide a construct of the structure F-S-L that is readily dispersible in water yet spontaneously incorporates into lipid bilayers, including the membranes of cells and enveloped viruses. Preferably, the biological entity is a cell or an enveloped virus. The $^{125}$I-labelled biological entity may be administered to the subject by injection. Preferably, the $^{125}$I-labelled biological entity is administered to the subject by intraperitoneal infusion or intravenous injection.

Preferably, F comprises an iodinated tyrosine (Tyr) residue. More, preferably the tyrosine (Tyr) residue is an N-carbonyl-Tyr residue. Most preferably, the tyrosine (Tyr) residue is an N-carbonyl-Tyr residue selected from the group consisting of: N—COH (N-formyl) Tyr residues and N—CO(CH$_2$)$_2$COOH Tyr residues.

In a third aspect the invention provides constructs of the structure F-S-L for use in the methods of the first aspect and the second aspect of the invention.

Preferably, the constructs are of the structure:

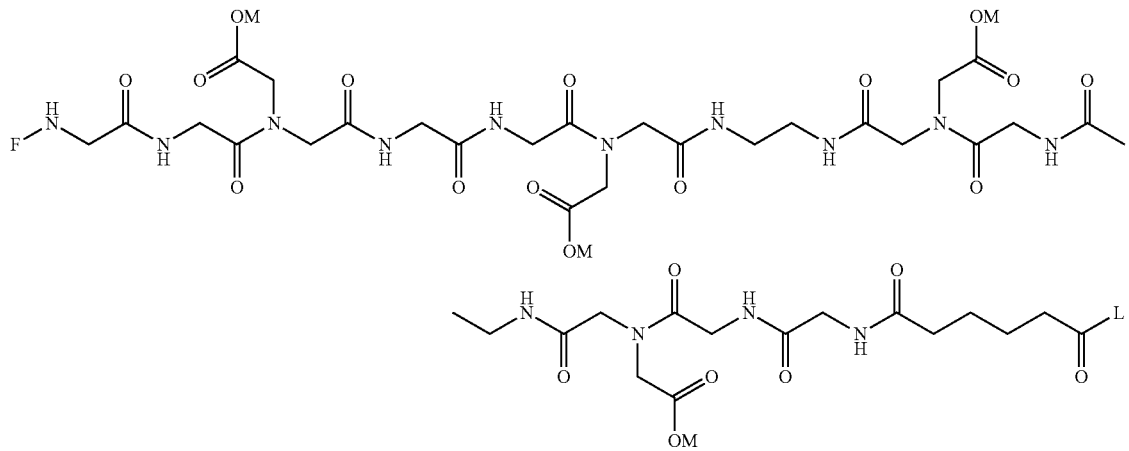

where M is H or CH$_3$ and * is other than H.

Preferably, F is a tyrosine residue selected from the group consisting of:
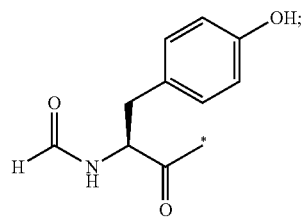
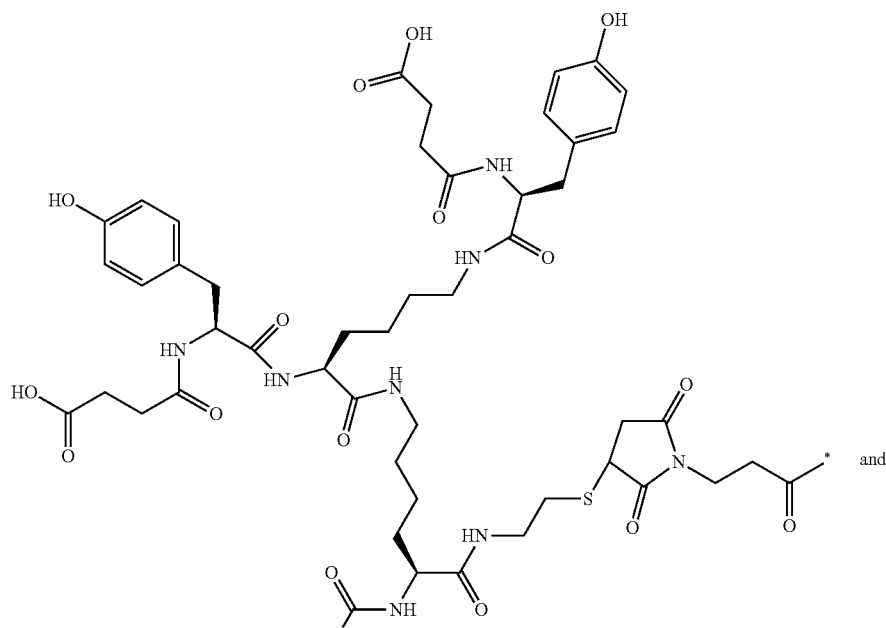
and
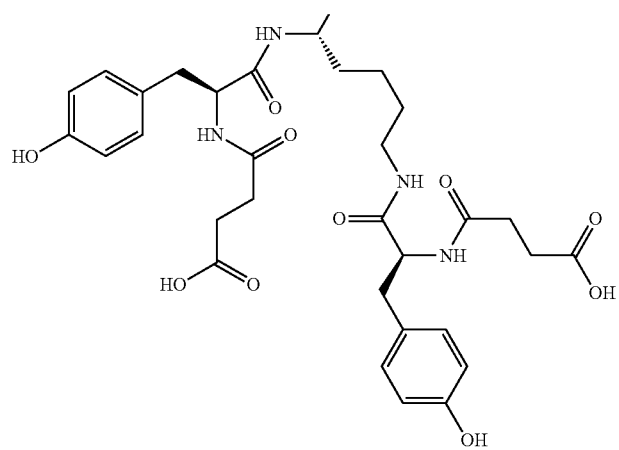

-continued

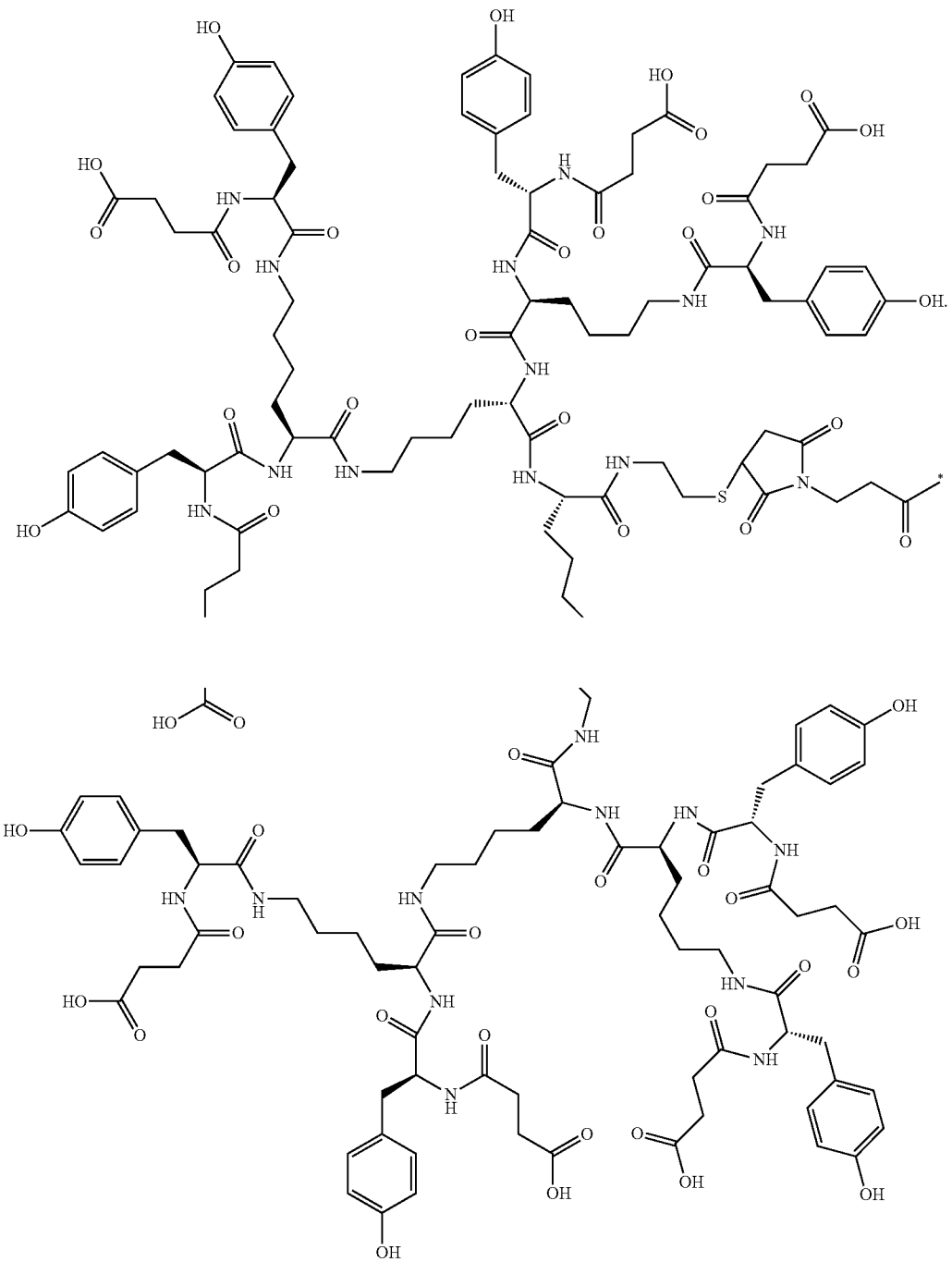

Preferably, L is phosphatidylethanolamine. More preferably, L is is selected from the group consisting of: 1,2-O-dioleoyl-sn-glycero-3-phosphatidylethanolamine (DOPE) and 1,2-O-distearyl-sn-glycero-3-phosphatidylethanolamine (DSPE). Most preferably, L is 1,2-O-dioleoyl-sn-glycero-3-phosphatidylethanolamine (DOPE).

In a first embodiment of the third aspect of the invention the constructs are of the structure N-formyl-(Tyr)$_n$-S-L where n is an integer from 1 to 6 inclusive. Preferably, n is 1 and the construct is of the structure:

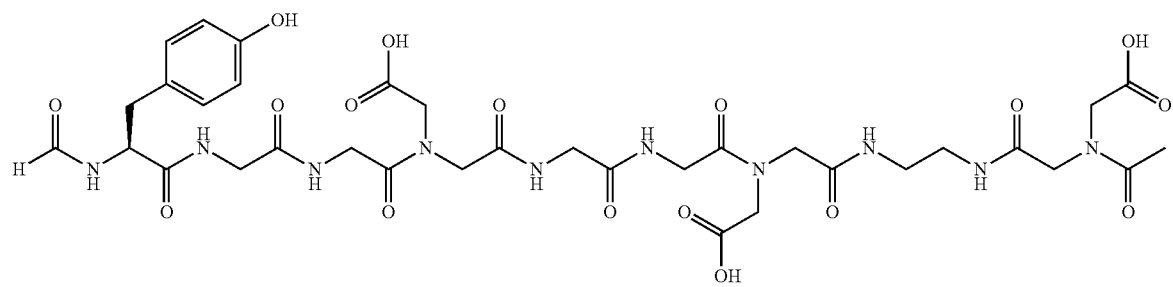
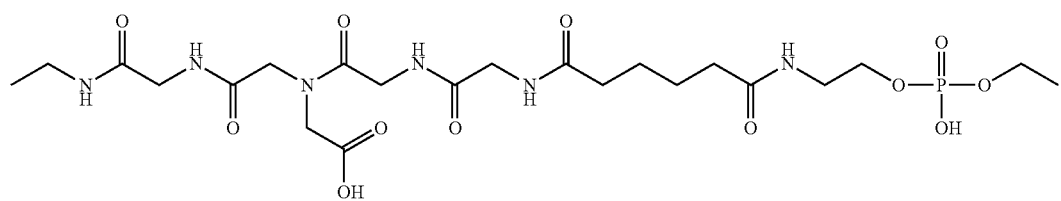
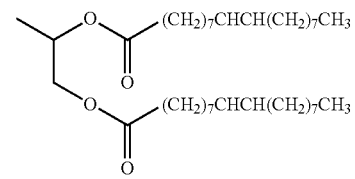
designated FSL-tyrosine.
In a second embodiment of the third aspect of the invention the constructs are of the structure:
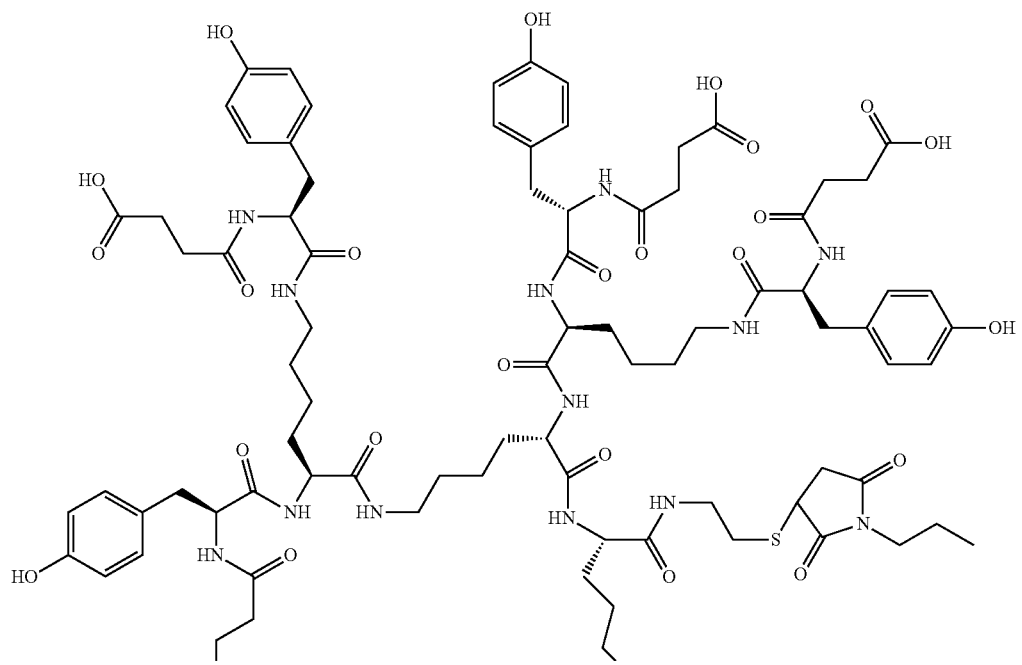

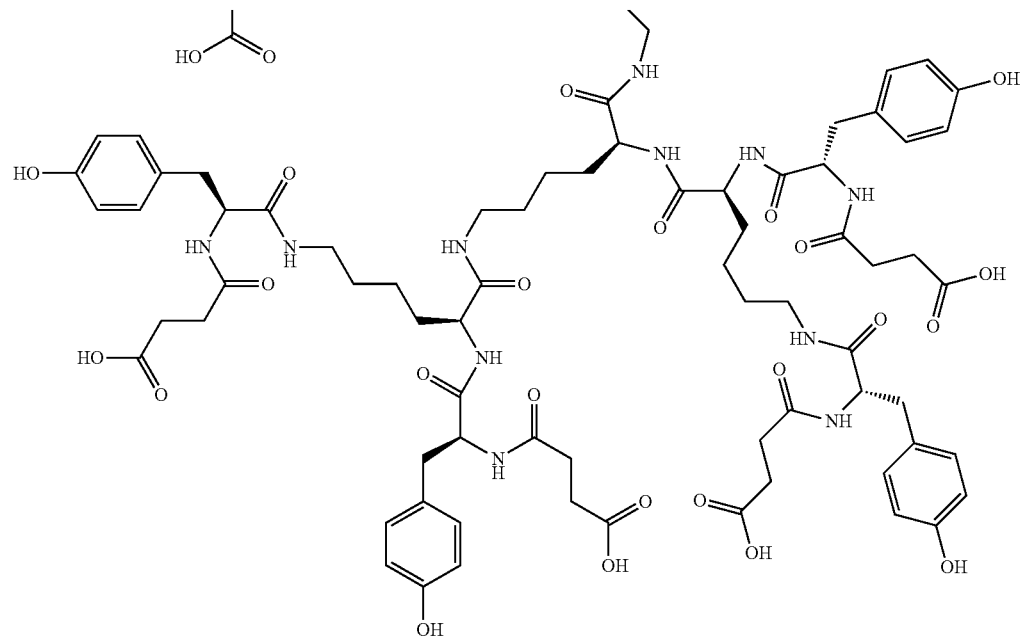
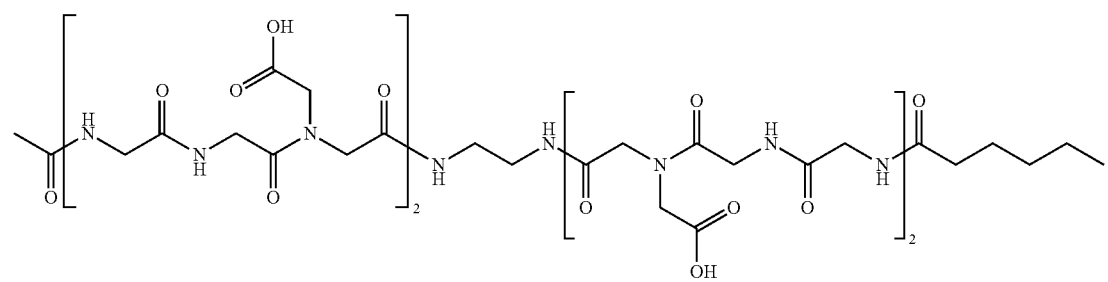
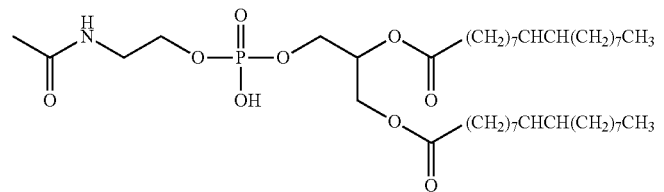
designated FSL-Tyr8.

In a second embodiment of the third aspect of the invention the constructs are of the structure:

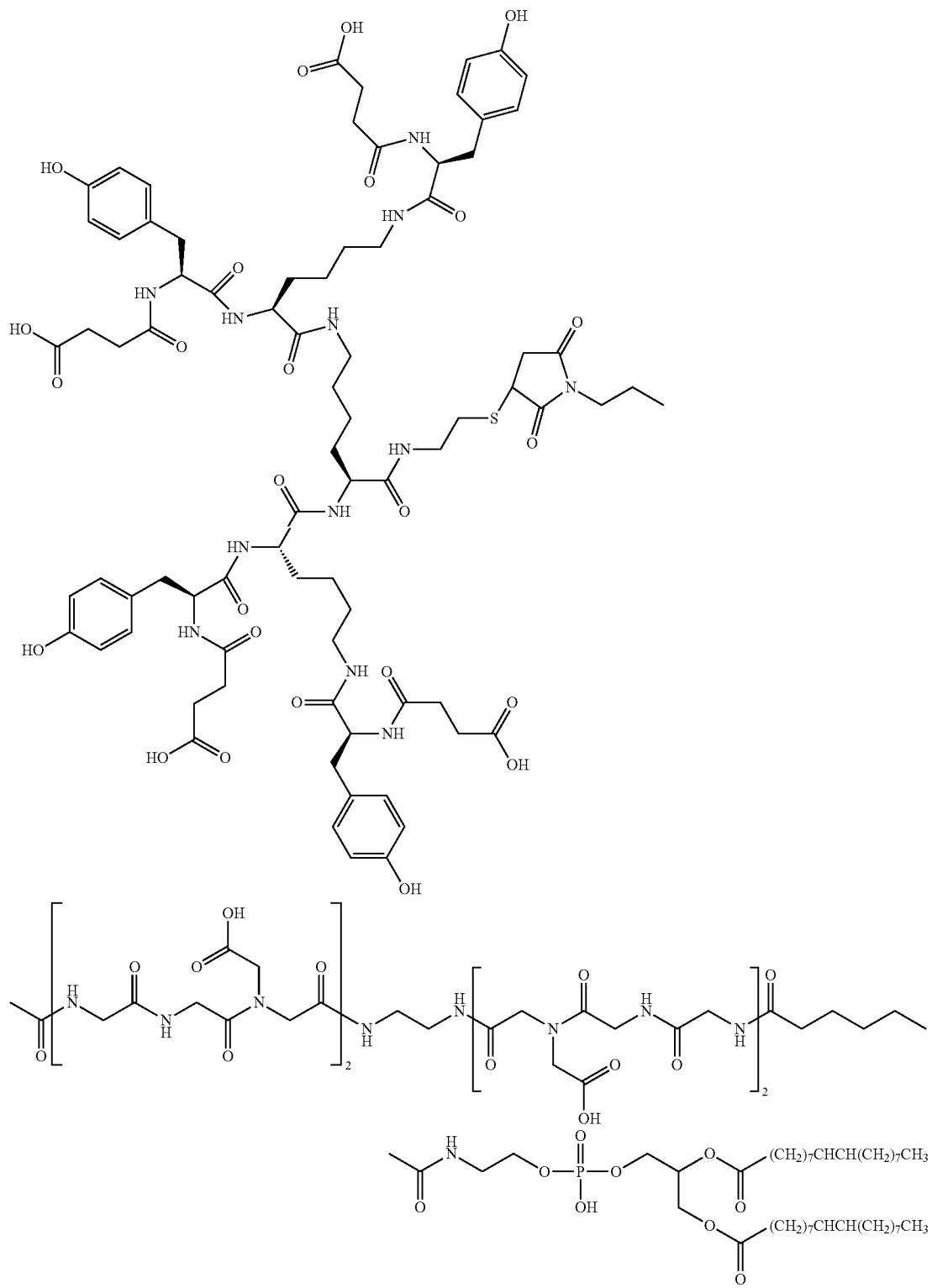

designated FSL-Tyr4.

In the description and claims of this specification the following acronyms, terms and phrases have the meaning provided:

"Aqueous suspension" means a suspension prepared in water with or without the addition of buffers or salts and specifically includes a suspension in saline.

"Biological entity" means a cell, multicellular structure or virus.

"Localised" means associated with a surface by non-covalent interactions and "localising" and "localisation" have a corresponding meaning.

"Monovalent cation (M)" means a counter ion having a positive charge of one (+1).

"Readily dispersible in water" means forms a stable, monophasic dispersion on contact with water at 25° C. in the absence of detergents or organic solvents.

"( )", "( )$_x$", "[ ]$_x$" and "[ ]" mean the group contained in the parentheses is repeated a number (x) of times. By way of illustration:

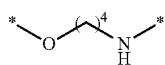

means the methylene group (—CH$_2$—) is repeated 4 times and the structure represented is equivalent to:

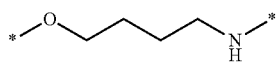 [SMILES: *NCCCCO*]

The terms "first", "second", "third", etc. used with reference to elements, features or integers of the subject matter defined in the Statement of Invention and Claims, or when used with reference to alternative embodiments of the invention are not intended to imply an order of preference.

The invention will now be described with reference to embodiments or examples and the figures of the accompanying drawings pages.

BRIEF DESCRIPTION OF DRAWINGS

The patent or application file contains at least one drawing executed in color. Copies of this patent or patent application publication with color drawing(s) will be provided by the Office upon request and payment of the necessary fee.

Figure 6:
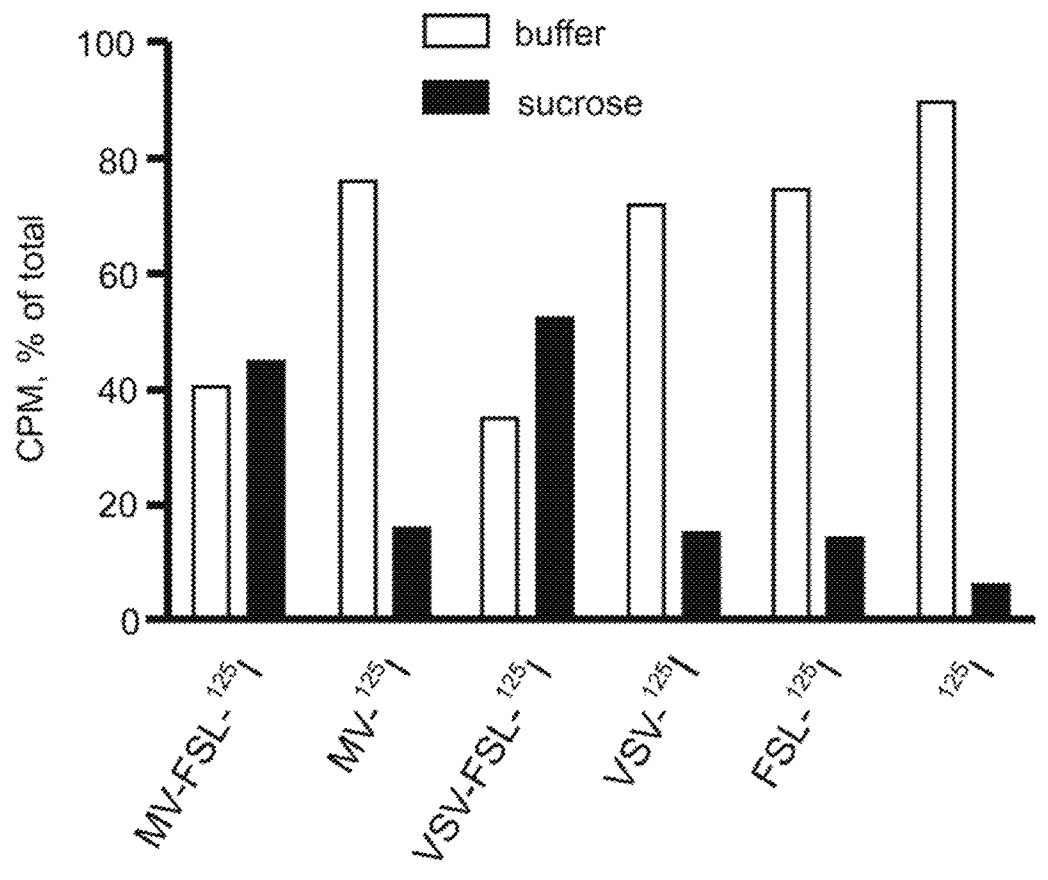

FIG. 6. VSV and MV incubated for 1 hour at room temperature with iodinated ($^{125}$I) FSL-tyrosine or Na$^{125}$I and harvested from the buffer or 20% sucrose portion of a step gradient tube following centrifugation for 75 min at 200 g.

The distribution of VSV modified by the iodinated ($^{125}$I) construct FSL-tyrosine is consistent with previously reported observations (Peng et al (2003)). Within an hour of administration the radiolabel localized to liver, spleen and bloodstream. Using the thyroid signal as an indicator it appears the modified virions are maintained in vivo for at least 4 hours. The localisation of modified virions to specific tissues can therefore be monitored quantitatively.

Materials and Methods

Trifluoroacetic acid (TFA), trifluoroethanol (TFE), 4-dimethylaminopyridine (DMAP), di-tert-Butyldicarbonate (Boc$_2$O), 1-hydroxybenzotriazole (HOBt), DIEA-diisopropylethylamine, O-(benzotriazol-1-yl)-N,N,N',N'-tetramethyluronium tetrafluoroborate (TBTU), Boc-Lys(Boc)-OH*DCHA and cysteamine were obtained from IRIS Gmbh (Germany). p-Nitrophenyl ester of N-ter-butyloxycarbonyl-tyrosine benzyl ether (Boc-Tyr(Bzl)-ONp) was obtained from Reanal (Hungary). Succinic anhydride and HF gas were obtained from Fluka.

Vesicular stomatitis virus human IFN☐ virus (VSV), and Measles virus MV-NIS (MV) were supplied by the Viral Vector production laboratory, Mayo Clinic. Influenza virus (H1N1) A/Puerto Rico/8/1934 (H1N1) human viruses were supplied by Institute of Virology RAS, Moscow. All native and labeled viruses were purified by ultracentrifugation in 20% sucrose. Age-matched (4-6 weeks old) female C57Bl mice (Harlan Sprague Dawley, Indianapolis, Ind.) were housed in a specific pathogen-free facility. All animal studies were approved by, and performed according to guidelines of a bioethics committee.

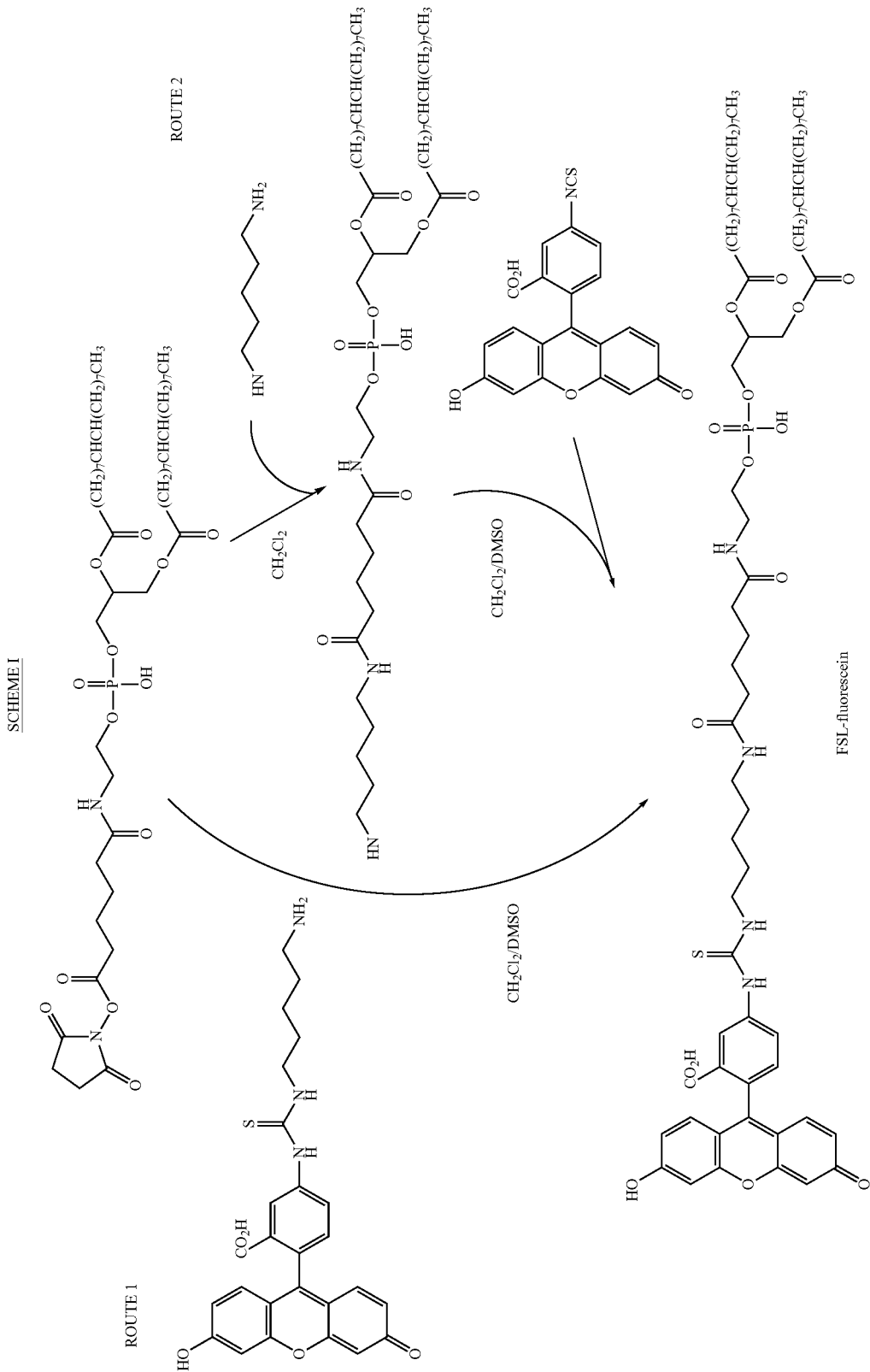

SCHEME II
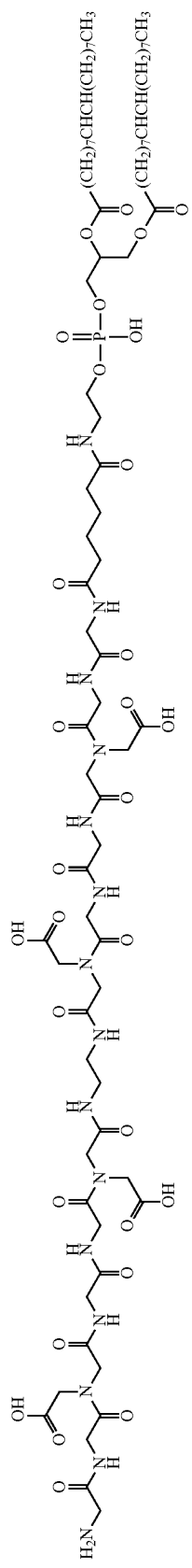
CMG$_2$-Ad-DOPE
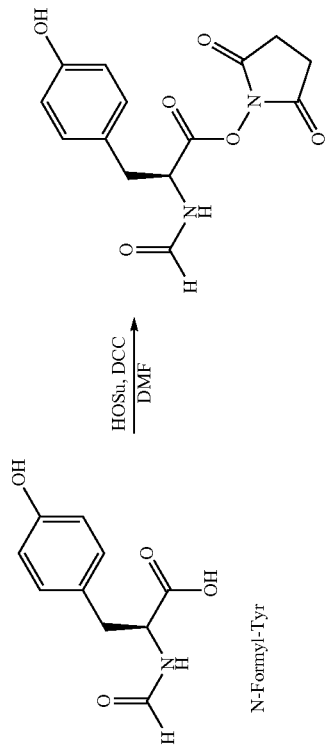
N-Formyl-Tyr
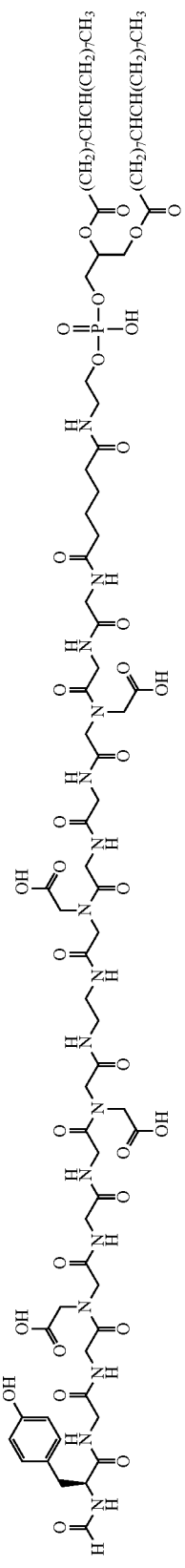
N-Formyl-Tyr-CMG$_2$-Ad-DOPE
[FSL-tyrosine]

Preparation of the Construct Designated FSL-Fluorescein

Figure 1:
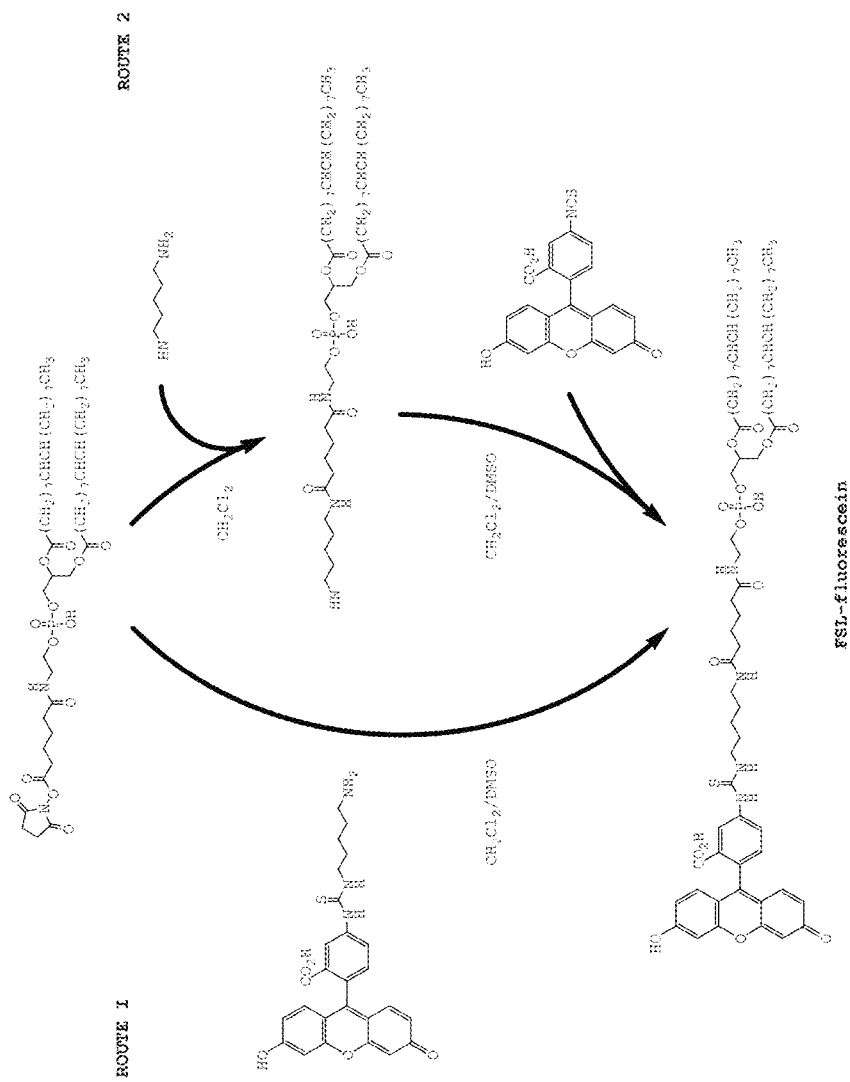
FIG. 1. Preparation of the construct desognated FSL-fluorescein according to route 1 or route 2 of Scheme I.

The construct was prepared according to Scheme I as presented in FIG. 1 as previously described (Korchagina et al (2008)) (Route 1) or as follows (Route 2):

Preparation of Activated 1,2-O-distereoyl-sn-glycero-3-phosphatidylethanolamine (DSPE) and Activated 1,2-O-dioleoyl-sn-glycero-3-phosphatidylethanolamine (DOPE) (L-A)

To a solution of bis(N-hydroxysuccinimidyl) adipate (A) (70 mg, 205 µmol) in dry N,N-dimethylformamide (1.5 ml) were added DOPE or DSPE (L) (40 µmol) in chloroform (1.5 ml) followed by triethylamine (7 µl). The mixture was kept for 2 h at room temperature, then neutralized with acetic acid and partially concentrated in vacuo.

Column chromatography (Sephadex LH-20, 1:1 chloroform-methanol, 0.2% acetic acid) of the residue yielded the activated lipid (L-A) (37 mg, 95%) as a colorless syrup; TLC (chloroform-methanol-water, 6:3:0.5): $R_f$=0.5 (DOPE-A), $R_f$=0.55 (DSPE-A).

$^1$H NMR (CDCl$_3$/CD$_3$OD, 2:1), δ:
DSPE-A—5.39 (m, 1H, —OCH$_2$—CHO—CH$_2$O—), 4.53 (dd, 1H, J=3.42, J=11.98, —CCOOHCH—CHO—CH$_2$O—), 4.33 (dd, 1H, J=6.87, J=11.98, —CCOOHCH—CHO—CH$_2$O—), 4.23 (m, 2H, PO—CH$_2$—CH$_2$—NH$_2$), 4.15 (m, 2H, —CH$_2$—OP), 3.61 (m, 2H, PO—CH$_2$—CH$_2$—NH$_2$), 3.00 (s, 4H, ONSuc), 2.81 (m, 2H, —CH$_2$—CO (Ad), 2.48 (m, 4H, 2×(—CH$_2$—CO), 2.42 (m, 2H, —CH$_2$—CO (Ad), 1.93 (m, 4H, COCH$_2$CH$_2$CH$_2$CH$_2$CO), 1.78 (m, 4H, 2×(COCH$_2$CH$_2$—) 1.43, 1.47 (2 bs, 40H, 20CH$_2$), 1.04 (m, 6H, 2CH$_3$).

DOPE-A—5.5 (m, 4H, 2×(—CH=CH—), 5.39 (m, 1H, —OCH$_2$—CHO—CH$_2$O—), 4.58 (dd, 1H, J=3.67, J=11.98, —CCOOHCH—CHO—CH$_2$O—), 4.34 (dd, 1H, J=6.61, J=11.98, —CCOOHCH—CHO—CH$_2$O—), 4.26 (m, 2H, PO—CH$_2$—CH$_2$—NH$_2$), 4.18 (m, 2H, —CH$_2$—OP), 3.62 (m, 2H, PO—CH$_2$—CH$_2$—NH$_2$), 3.00 (s, 4H, ONSuc), 2.8 (m, 2H, —CH$_2$—CO (Ad), 2.50 (m, 4H, 2×(—CH$_2$—CO), 2.42 (m, 2H, —CH$_2$—CO (Ad), 2.17 (m, 8H, 2×(—CH$_2$—CH=CH—CH$_2$—), 1.93 (m, 4H, COCH$_2$CH$_2$CH$_2$CH$_2$CO), 1.78 (m, 4H, 2×(COCH$_2$CH$_2$—), 1.43, 1.47 (2 bs, 40H, 20CH$_2$), 1.04 (m, 6H, 2CH$_3$).

Condensation of Activated DOPE (L-A) with Cadaverine

To a solution of cadaverine (110 µl, 940 µmol) in dichloromethane (3 mL) a solution of activated DOPE (L-A) (90 mg, 93 µmol) in dichloromethane (CH$_2$Cl$_2$) (0.5 mL) was added. The mixture was kept for 0.5 h at room temperature and then portions of 180 µL of acetic acid were added over the course of 5 minutes. The mixture was concentrated in vacuo and the residue chromatographed (Sephadex LH-20, 1:2 chloroform-methanol) to provide 74 mg (84%) of DOPE-Ad-cadaverine, $R_f$ 0.35 (ethyl acetate-isopropanol-water, 2:3:1)

$^1$H NMR (700 MHz, [D$_3$]CHCl$_3$/[D$_4$]CH$_3$OH 1:1, 30° C.): δ, ppm 5.50 (m, 4H, 2×(—C$\underline{H}$=C$\underline{H}$—), 5.38 (m, 1H, —OCH$_2$—CHO—CH$_2$O—), 4.59 (dd, 1H, J=6.6, $J_{gem}$=11.8, $\underline{H}$HC—O—C(O)—), 4.35 (dd, 1H, J=3.2, $J_{gem}$≈11.8, H$\underline{H}$C—O—C(O)—), 4.14 (m, 2H, —OCH$_2$—O—P—), 4.08 (m, 2H, —P—O—CH$_2$—CH$_2$—NH—), 3.58 and 3.39 (2m, 2×2H, N—C$\underline{H}$$_2$—CH$_2$—O—P— and N—CH$_2$—(CH$_2$)$_3$—CH$_2$NH$_2$) 3.05 (m, 2H, N—CH$_2$—(CH$_2$)$_3$—C$\underline{H}$$_2$NH$_2$), 2.48 (m, 4H, 2×(—C$\underline{H}$$_2$—CO), 2.39 (m, 4H, COCH$_2$CH$_2$CH$_2$CH$_2$CO), 2.19 (m, 8H, 2×(—CH$_2$—CH=CH—C$\underline{H}$$_2$—), 1.8, 1.72, 1.58 (3m, 10H, 2H, 2H, COCH$_2$CH$_2$CH$_2$CH$_2$CO, 2×(COCH$_2$CH$_2$—), and —N—CH$_2$—(C$\underline{H}$$_2$)$_3$—CH$_2$NH$_2$), 1.42, 1.46 (2 bs, 40H, 20 CH$_2$), 1.05 (m ~t, J≈47 Hz 6H, 2 CH$_3$).

Condensation of DOPE-Ad-Cadaverine with Fluorescein Isothiocyanate (FITC)

To a solution of fluorescein isothiocyanate (FITC) (16.3 mg, 42 µmol) in DMSO (0.3 mL) a solution of DOPE-Ad-cadaverine (40.2 mg, 42 µmol) in dichloromethane (0.5 mL) and triethylamine (7 µL) were added. The mixture was kept for 2 h at room temperature and then partially concentrated in vacuo. The residue was chromatographed (Sephadex LH-20, 1:2 chloroform-methanol) to provide 8 mg (~8%) of FSL-fluorescein (triethylamine(Et$_3$N) salt) and about 40 mg of crude FSL-fluorescein. The latter was chromatographed (silica gel, ethyl acetate-isopropanol-water, 6:3:1) to yield 24.3 mg (~40%) of FSL-fluorescein (sodium (Na) salt). The NMR spectra of the obtained salts of FSL-fluorescein were identical to those of the corresponding salts obtained via Route I.

Preparation of the Construct Designated FSL-Tyrosine (FSL-Tyr)

Figure 2:
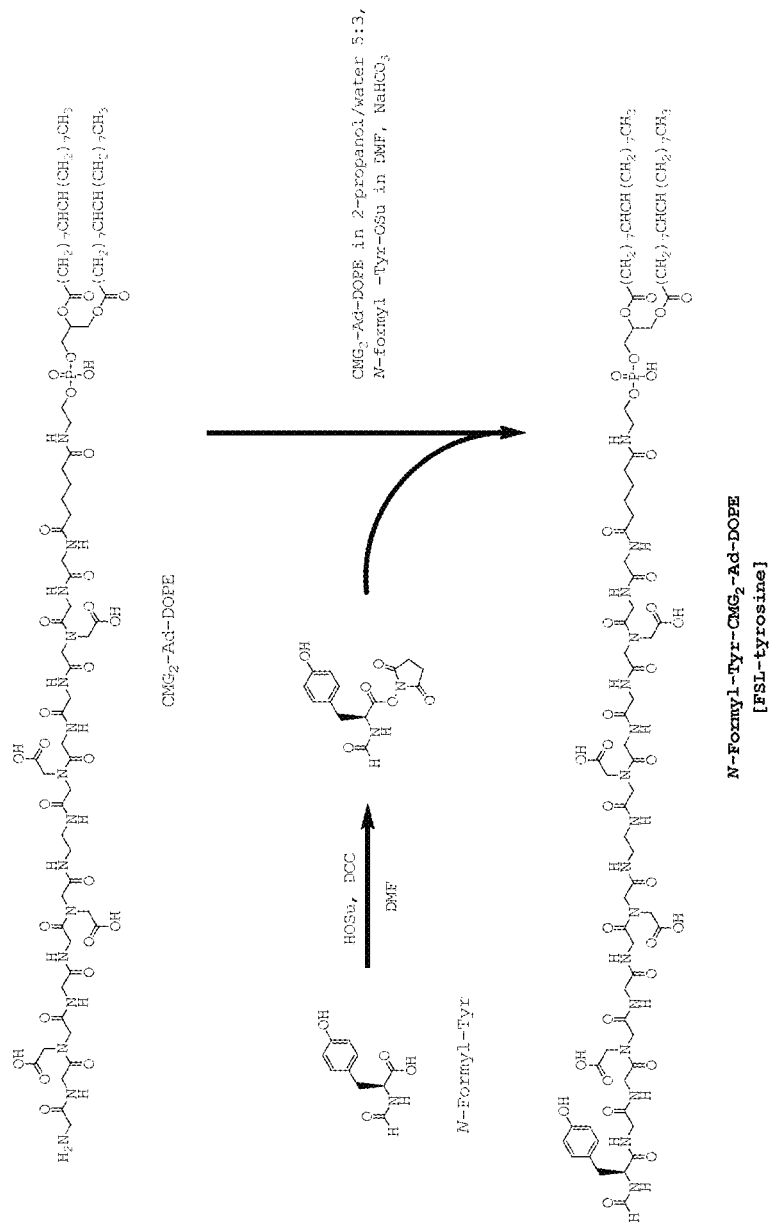
FIG. 2. Preparation of the construct designated FSL-tyrosine according to Scheme II.

The construct was prepared according to Scheme II as presented in FIG. 2 as follows:

Preparation of N-Oxysuccinimide Ester of N-Formyl-Tyrosine

N-formyl-tyrosine (81.2 mg) was dissolved in DMF (1.6 mL) followed by the addition of N-hydroxysuccinimide (60 mg) and dicyclohexylcarbodiimide (80 mg in 0.8 mL DMF). The mixture was stirred for 2.5 h at room temperature and the precipitate of N-dicyclohexylurea filtered off. N-formyl-tyrosine ($R_f$ 0.53), N-formyl-tyrosine N-oxysuccinimide ester ($R_f$ 0.64) (CHCl$_3$/MeOH/AcOH; 40:20:3 (v/v/v)).

Preparation of N-Formyl-Tyrosine-CMG$_2$-Ad-DOPE

The intermediate CMG$_2$-Ad-DOPE was prepared as previously described (Bovin et al (2009)). CMG$_2$-Ad-DOPE (250 mg) was dissolved in 5 mL of water and 3 mL of methanol. A solution of the N-oxysuccinimide ester of N-formyl-tyrosine, 1 mL of DMF and 0.647 mL of 1 M NaHCO$_3$ were then added. The mixture was stirred for 45 min, than acidified with 0.2 mL of AcOH. The solution was evaporated in vacuo to a minimal volume. Following the addition of 200 µL of Py, the residue was separated on an LH-20 column (170 ml) (2-propanol/water; 1:2+0.05 M Py.HOAc. Fractions containing pure product were combined, evaporated and freeze-dried.

The residue (Na$_1$, Py$_1$ salt) was dissolved in 3 mL of water. A 60 µL volume of 8 mM NH$_3$ was then added and the resulting solution freeze-dried. Yield 239 mg (91%). $R_f$=0.53 (CHCl$_3$/MeOH/water; 3:6:1 (v/v/v)). Brutto formula C91H156N20NaO33P. molecular weight as Na$_1$(NH$_4$)$_4$ salt—2112.3. MALDI TOF mass-spectrum (FLEX-PC, DHB) m/z: 2044 M+Na; 2060 M+K; 2066 M+2Na; 2082 M+Na+K; 2088 M+3Na; 2098 M+2K. $^1$H-NMR spectrum, δ ppm (5 mg/ml in CD$_3$OD/D$_2$O 1:2, 303K, 800 MHz): 8.238 (s, 1H, $\underline{H}$(CO)N), 7.324 and 6.993 (d, 2×2H, J=8.2 Hz, p-C$_6$$\underline{H}$$_4$), 5.507 (m, 4H, 2 C$\underline{H}$=C$\underline{H}$), 5.453 (m, 1H, OCH$_2$—C$\underline{H}$—CH$_2$O), 4.823 (~t, 1H, J=7.2 Hz, αCH of tyrosine), 4.615 (dd, 1H, J$_1$=12 Hz, J$_2$=2 Hz, OCH$_2$—CH—C$\underline{H}$O), 4.442-4.063 (37H, 32H of CMG$_2$, OC$\underline{H}$$_2$—CH—C$\underline{H}$O and OC$\underline{H}$$_2$CH$_2$N), 3.523-3.478 (4H, NC$\underline{H}$$_2$CH$_2$N), 3.251 (dd, 1H, J$_\beta$=13.8 Hz, J$_\alpha$=6.3 Hz, βCH of tyrosine), 3.138 (dd, 1H, J$_\beta$=13.8 Hz, J$_\alpha$=8.1 Hz, βCH of tyrosine), 2.532-2.453 (m, 8H, 4 C(O)C$\underline{H}$$_2$), 2.189 (m, 8H, 2 C$\underline{H}$$_2$CH=CHC$\underline{H}$$_2$), 1.802 (m, 4H, 2 C(O)CH$_2$C$\underline{H}$$_2$ of adipic fr.), 1.771 (m, 4H, 2 C(O)CH$_2$CH$_2$ of DOPE), 1.514, 1.477 and 1.459 (m, 40H, 20 CH$_2$ of DOPE), 1.064 (t, 6H, J=7 Hz, 2 CH$_3$).

Preparation of the Constructs Designated FSL-Tyr4 and FSL-Tyr8

The constructs were prepared according to Scheme III as presented in FIGS. 3A to 3E follows:
Solid-Phase Synthesis (SPS) of Multivalent Tyrosine Dendrons
Solid-phase reactions were performed manually in 50, 30 or 20 mL polypropylene (PP) syringes (BD, USA) equipped with PP frit at the bottom and 19 G disposable needle used for connecting Luer outlet to the waste flask via the septum stopper during washing steps. The needle was changed for Luer stopper in the course of coupling and deprotection steps performed with occasional shaking. Volumes of solvents and reagent solutions used for every SPS operation were circa 10 mL/1 g of starting resin initially, the volume gradually increased to accommodate swelling of the peptide resin (PR) due to incorporation of peptide material. By default, during the course of all repeated coupling steps DMAP was introduced 30 to 60 min before the reactions were terminated (10 mol % with respect to resin loading). Completeness of the coupling reactions was monitored by the qualitative ninhydrin reaction (Kaiser et al (1970)). Resin loadings (mmol/g) were calculated on the basis of respective PR weight gain.

Figure 3A:
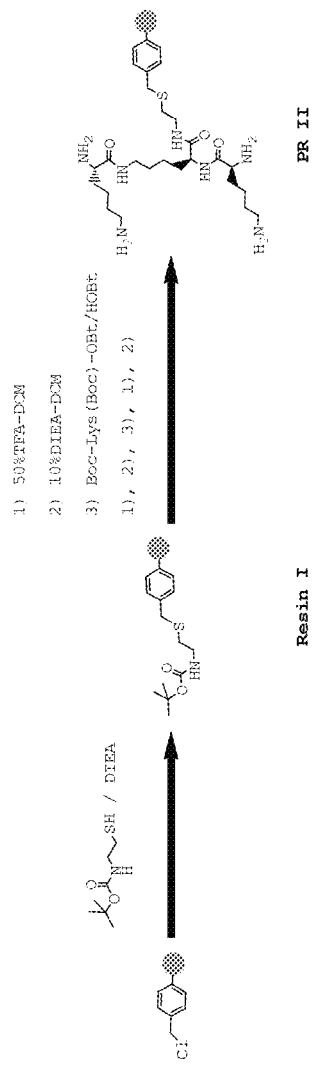
FIGS. 3A to 3E. Preparation of the constructs designated FSL-Tyr4 (3A, 3D and 3E) and FSL-Tyr8 (3A, 3B and 3C) according to scheme III.

Preparation of Boc-NHCH$_2$CH$_2$SCH$_2$-Resin (Resin I) and (Lys)$_2$-Lys-NHCH$_2$CH$_2$SCH$_2$-Resin (PR II) (Scheme III-Part I, FIG. 3A)

A vigorously stirred slurry of finely grounded cysteamine (1.05 g, 13.6 mmol) in DMF (10 ml) was treated with Boc$_2$O (3.56 g, 16.4 mmol) until starting material completely dissolved (circa 0.5 hrs). (The dissolution may require brief heating at 40 to 50° C.) To the solution of N-Boc-cysteamine obtained diisopropylethylamine (DIEA; 1.5 mL, 7 mmol), NaI (102 mg, 0.7 mmol) and DMF were added to final volume of 60 mL, followed by 10 g (6.8 mmol) of chloromethylated copolymer of styrene; 1% divinylbenzene (0.68 meq of Cl/g; Peptide Institute Inc., Japan). The alkylation reaction was allowed to proceed for 2 hours at room temperature and then at 50° C. overnight. The resin was washed with IPA-DMF (2:1), DMF, IPA-DMF (2:1), DMF, IPA-DMF (2:1), dichloromethane (DCM), IPA-DCM (1:1, v/v), DCM and dried in vacuum to provide 10.96 g Boc-NHCH$_2$CH$_2$SCH$_2$-resin (Resin I) with loading of 0.61 mmol/g estimated from the observed weight gain and 0.03 mmol/g of residual chloromethyl functions quantitated according to the published procedure (Tam (1985)). A 2 g (1.22 mmol) amount of the Resin I was treated with TFA-DCM (1:1, v/v) for 1 min and 25 min, DCM, DMF-IPA (1:2), 2 times [DIEA (5% v/v) in DCM, DMF-IPA (1:2)] followed by solution of Boc-Lys(Boc)-OBt. The latter was prepared by dissolving 0.63 g, (1.2 mmol) of Boc-Lys(Boc)-OH*DCHA in the solution of TBTU (0.35 g, 1.1 mmol) in DMF (5 mL) with sonication. To an essentially clean solution 0.16 g, (1.2 mmol) of HOBt and DMF were added to provide a final volume of 15 mL. Coupling was terminated after 2 hours and the resin was washed with DIEA (5% v/v) in DCM, DMF-IPA (1:2) and the residual amino groups were acetylated with Ac$_2$O-DMF (1:4 v/v) until negative ninhydrin test obtained. The resin was treated twice with TFA-DCM (1:1, v/v) for 1 min and 40 min, DCM, DMF-IPA (1:2), 2 times [5% (v/v) DIEA in DCM, DMF-IPA (1:2)] and coupling carried out for 5 hours with Boc-Lys(Boc)-OBt solution obtained as described above from respective DCHA-salt (1.27 g, 2.4 mmol), TBTU (0.69 g, 2.16 mmol) and HOBt (0.16 g, 1.2 mmol). The resin was washed with 5% (v/v) DIEA in DCM, DMF-IPA (1:2) and coupling was repeated with the fresh solution of Boc-Lys(Boc)-OBt at 50° C. overnight. The resin washed with DMF-IPA (1:2), DCM, DCM-IPA (1:2, v/v)] was treated with TFA-DCM (1:1, v/v) for 1 min and 60 min, DCM, DMF-IPA (1:2), 2 times [5% (v/v) DIEA in DCM, DCM-IPA (1:2)] and dried in vacuum to constant weight; yield 2.81 g of PR II with loading 1.7 mmol NH$_2$/g.

Figure 3B:
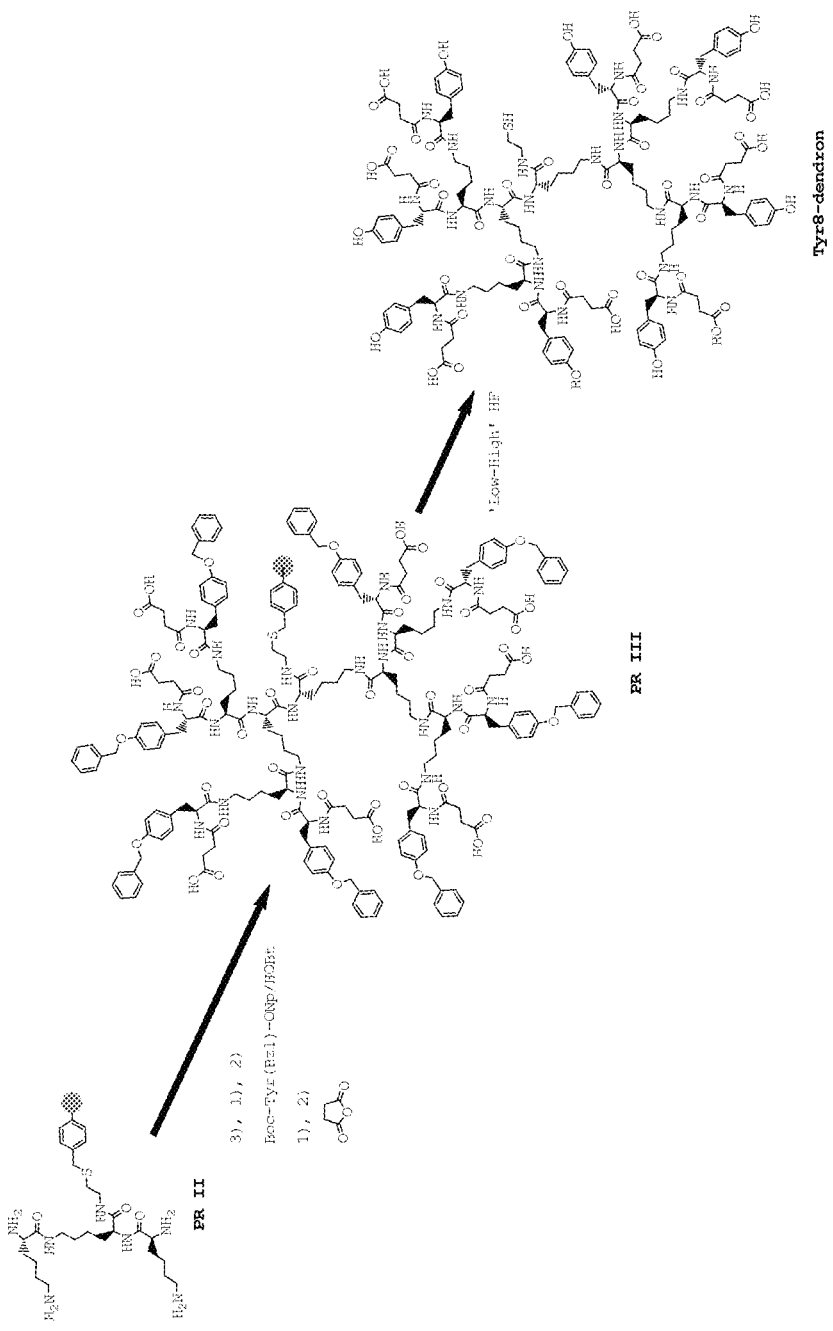

Preparation of [Suc-Tyr (Bzl)]$_8$-Lys)$_4$-(Lys)$_2$-Lys-NHCH$_2$CH$_2$SCH$_2$-Resin (PR III) and (Suc-Tyr)$_8$-(Lys)$_4$-(Lys)$_2$-Lys-NHCH$_2$CH$_2$SH (Tyr$_8$-dendron) (Scheme III-Part 2A, FIG. 3B)

1 g (1.7 mmol) of dry PR II was treated with oxybenzotriazol ester solution prepared as described above from Boc-Lys(Boc)-OH*DCHA-salt (2.1 g, 3.9 mmol), TBTU (1.12 g, 3.5 mmol) and HOBt (0.24 g, 1.7 mmol) for 6 hours at 50° C. A second coupling was performed with double quantity (7.8 mmol) of the active ester at 50° C. overnight. Ninhydrin negative resin was washed with DCM, DCM-IPA (1:2), deprotected (1 min and 70 min) and neutralized as above. The next coupling was repeated 3 times with a solution of 6.4 g (13 mmol) of Boc-Tyr(Bzl)-ONp (Reanal, Hungary) in 10 mL DMF containing 0.45 g (3.3 mmol) HOBt. The first coupling was performed at room temperature for 5 hours, the second and the third couplings were performed at 50° C. for 6 and 12 hours, respectively. The ninhydrin-negative resin obtained was washed with 2 times [DMF-IPA (1:2), 5% (v/v) DIEA in DCM], DCM, DCM-IPA (1:2), deprotected (1 min and 60 min) and neutralized as above. The final acylation with 1 g (10 mmol) of succinic anhydride (Pierce) in DMF (10 mL) was carried out for 5 hours at room temperature and repeated with fresh reagent at 50° C. for 6 and 12 hours. The PR III was thoroughly washed with DMF-IPA (1:2), DCM, DMF, DCM-IPA (1:2), DCM to remove traces of p-nitrophenol and dried in vacuo; yield 1.52 g. A part of the PR III (1.05 g) was subjected to 'low-high' HF cleavage procedure (Tam and Merrifield, (1987)). "Low-HF" procedure details: 12 mL DMS/5 mL HF, 0° C., 2 hrs. Volatiles were removed in vacuum and the solids were washed repeatedly with DCM and EtOAc to ensure that any traces of benzyldimethylsulfonium by-product are removed completely, and dried. "High-HF" cleavage was performed in 10 mL of HF-p-cresol (9:1, v/v) for 2 h at 0° C. After HF removal the residue was triturated with Et$_2$O and washed 3 times [EtOAc, Et$_2$O] (both solvents contained 1% (v/v) of mercaptoethanol) and peptide material was extracted with 3 times 6 mL of DCM-TFE (2:1). The extract was concentrated in vacuum, peptide precipitated with Et$_2$O, centrifuged and re-precipitated two times with Et$_2$O from a minimum volume of DCM-TFE (2:1). Yield—170 mg of Tyr$_e$-dendron which was characterized by ESI-MS and NMR and used in the next step without further purification. ESI-MS (Negative mode, 20% MeOH), m/z: 1539.3 [M-2H]$^{2-}$; 1025.9 [M-3H]$^{3-}$. Calculated MW 3080.4

Figure 3C:
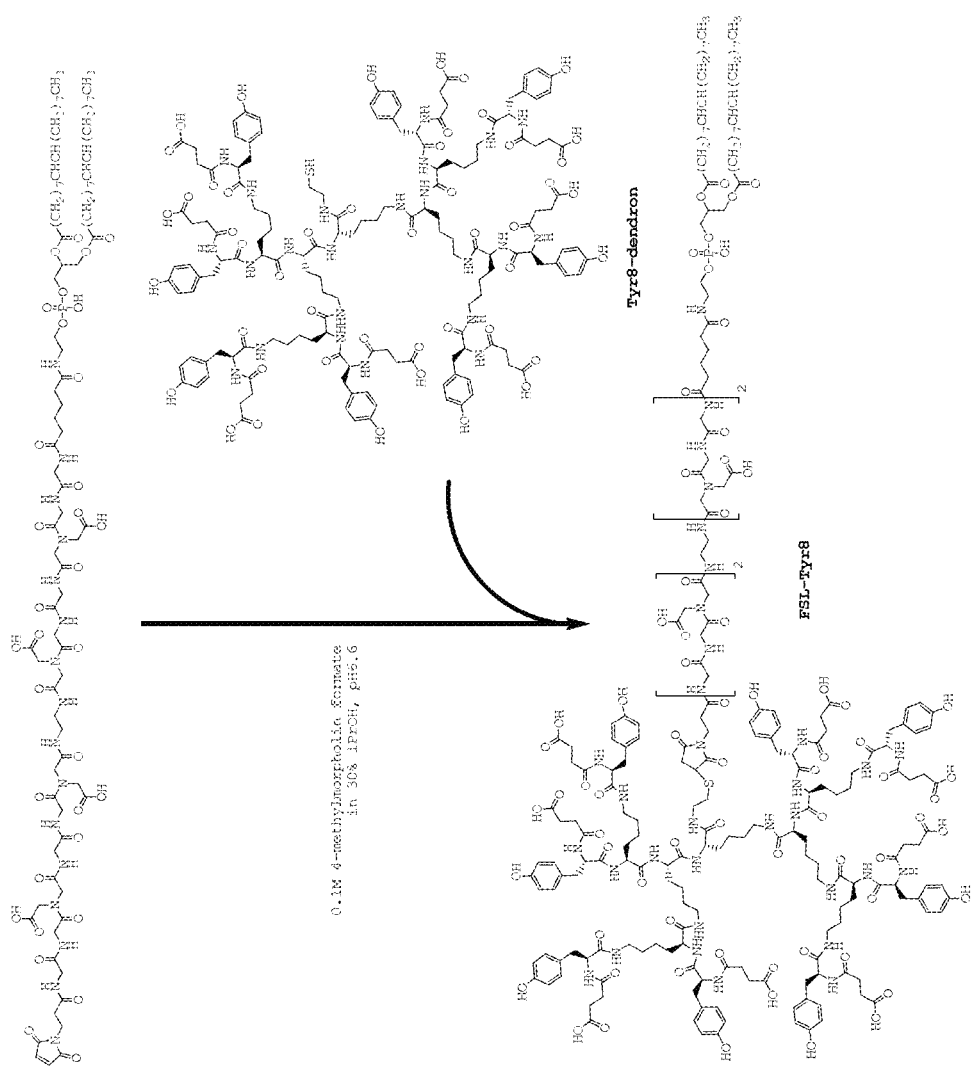

Preparation of (Suc-Tyr)$_8$-(Lys)$_4$-(LYS)$_2$-LYS-NHCH$_2$CH$_2$S-Mal-βAla-CMG$_2$-Ad-DOPE (ESL-Tyr8) (Scheme III-Part 3A, FIG. 3C)

A solution of a (Suc-Tyr)$_8$-(Lys)$_4$-(Lys)$_2$-Lys-NHCH$_2$CH$_2$SH (20.7 mg, 6.2 µmol) in 6 mL 0.1M NMM formate in 30% aqueous isopropyl alcohol (30% IPA) pH 6.6 was combined with 1.2 mL of the same buffer, in which 9.02 mg, 4.5 µmol of Mal-βAla-CMG$_2$-Ad-DOPE (Bovin et al (2009)) were dissolved. The clear solution was kept overnight at room temperature and lyophilized. The residue thus obtained was trituated with IPA (1 mL) and the mixture was sonicated until uniform suspension was obtained (circa 10 min). The slurry was then transferred into an Eppendorf tube and centrifuged. The precipitate was further washed with IPA, re-dissolved in 200 μL 20% IPA, re-precipitated with 1 mL of IPA and washed alternately with EtOH and IPA (2 times 200 μL of each, ultrasonic bath followed by centrifugation). The wet precipitate was dissolved in 2 ml of water and lyophilized; yield 20.2 mg (88%) of amorphous white powder. ESI-MS (Negative mode, 20% IPA), m/z: 1686.6 $[M-3H]^{3-}$, 1264.7 $[14-4H]^{4-}$; 1271.4 $[M-4H+ Na]^{4-}$; Calculated MW 5062.6.

Figure 3D:
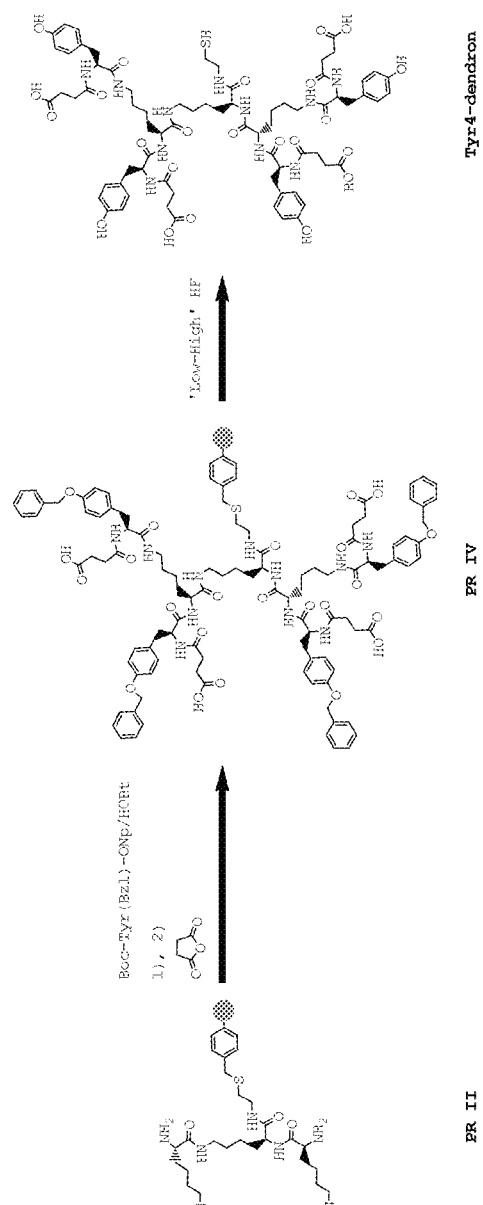

Preparation of (Suc-Tyr)$_4$-(Lys)$_2$-Lys-NHCH$_2$CH$_2$SCH$_2$-Resin (PR IV) and (Suc-Tyr)$_4$-(Lys)$_2$-Lys-NHCH$_2$CH$_2$SH (Tyr$_4$-dendron) (Scheme III-Part 2B, FIG. 3D)

The title PR IV was assembled on PR II (1 g, 1.7 mmol) via two chain extension steps detailed in the preparation of PR III applying the same molar excesses of activated species with respect to resin. Yield of PR IV—1.39 g. A part of the PR IV (1.11 g) obtained was subjected to 'low-high' HF cleavage procedure as specified above for octavalent homologue to yield 117 mg of Tyr$_4$-dendron. ESI-MS (Negative mode, 30% IPA), m/z: 1513.8 $[M-H]^-$; 757.5 $[M-2H]^{2-}$ Calculated MW 1514.7

Figure 3E:
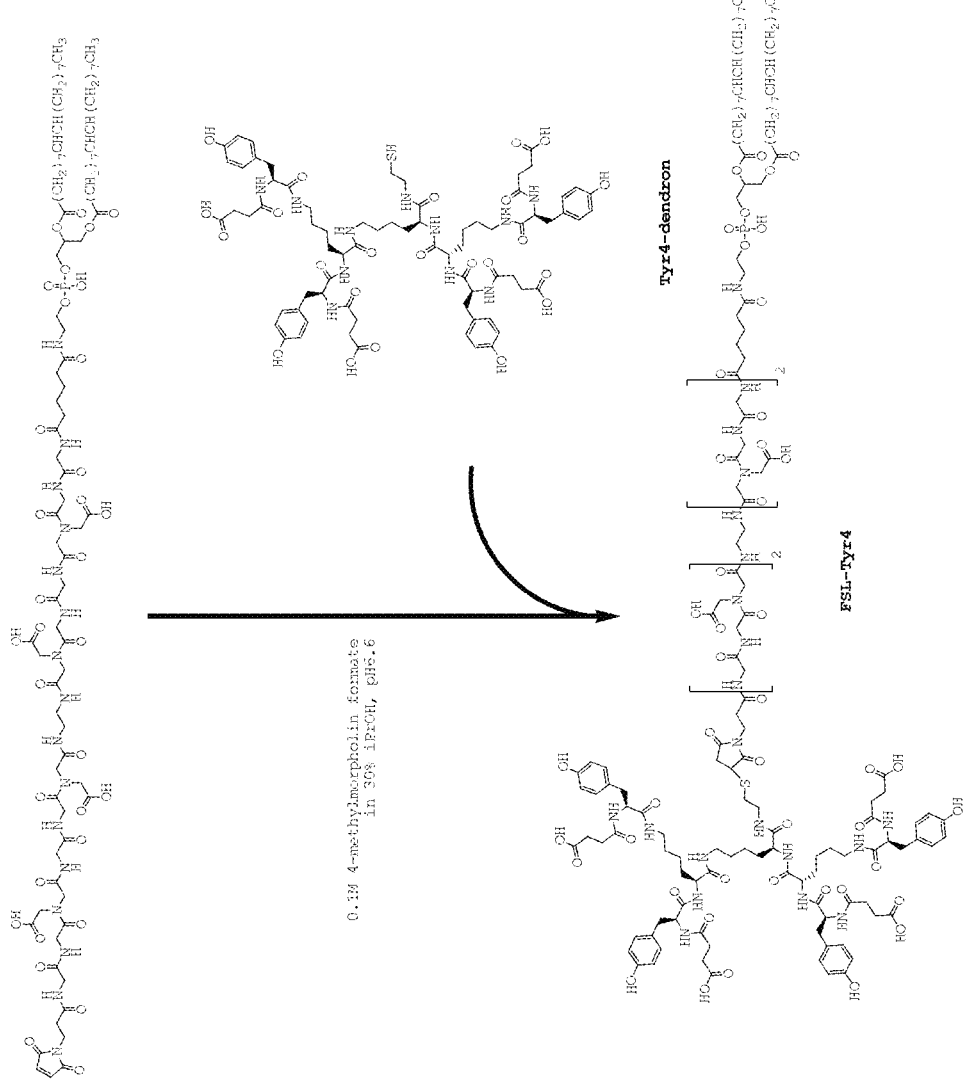
Figure 4:
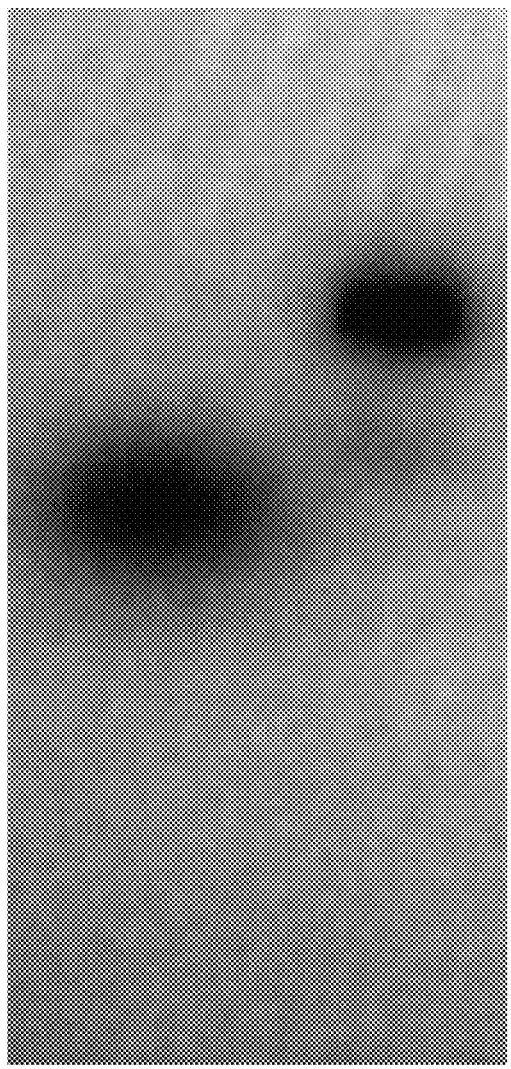
FIG. 4. Autoradiograph of free Na$^{125}$I (left lane) and iodinated ($^{125}$I) FSL-tyrosine (right lane) run on 15% acrylamide gel SDS-PAGE in non-reducing sample buffer.
Figure 5:
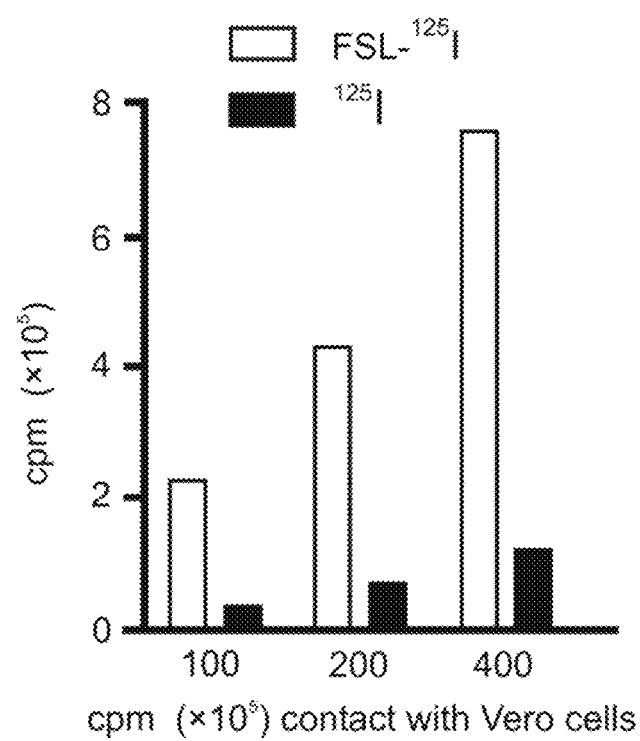
FIG. 5. Iodinated ($^{125}$I) FSL-tyrosine insertion into Vero cells. Vero cells 5×10$^5$ cells/well were contacted with either iodinated ($^{125}$I) FSL-tyrosine or $^{125}$I (of equal cpm) and incubated for 2 hours at 37° C. Washed cells were lysed then radioactivity measured.
Figure 7:
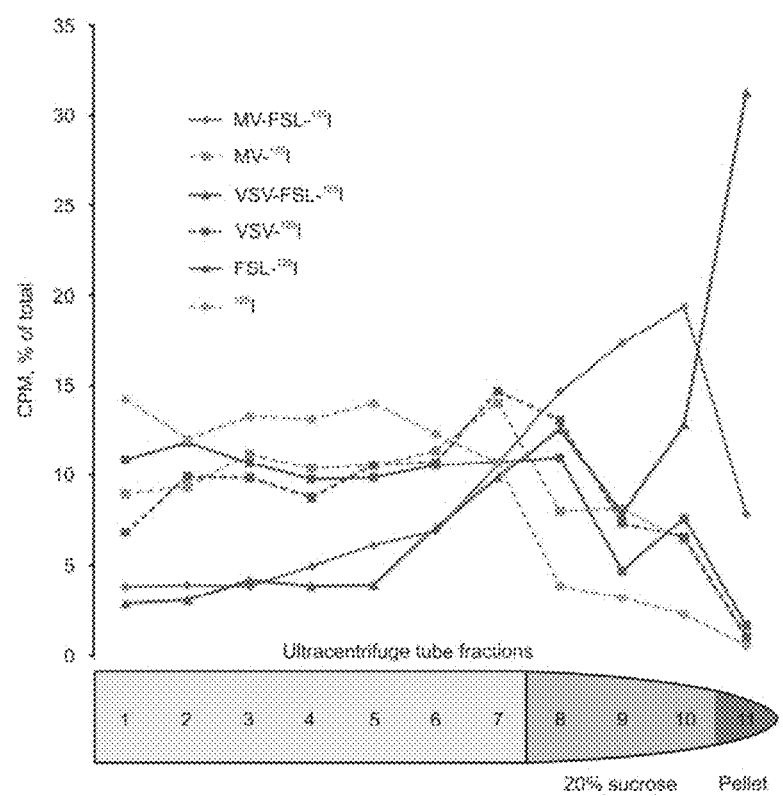
FIG. 7. Ultracentrifuge 20% sucrose fractionations of iodinated ($^{125}$I) FSL-tyrosine or $^{125}$I labeled VSV and MV.

Preparation of (Suc-Tyr)$_4$-(Lys)$_2$-Lys-NHCH$_2$CH$_2$S-Mal-βAla-CMG$_2$-Ad-DOPE (FSL-Tyr4)(Scheme III-Part 3B, FIG. 3E)

The construct FSL-Tyr4 was obtained according to standard conjugation procedure exemplified for the construct FSL-Tyr8 as described above. Reaction of 15.1 mg (10 μmol) of (Suc-Tyr)$_4$-(Lys)$_2$-Lys-NHCH$_2$CH$_2$SH with 13.23 mg (6.6 μmol) of Mal-βAla-CMG$_2$-Ad-DOPE in 5.5 mL of 30% v/v IPA containing 0.1M NMM formate, pH 6.6 yielded 17.5 mg (76%) of the desired construct FSL-Tyr4. ESI-MS (Negative mode, 30% IPA), m/z: 1746.7 $[M-2H]^{2-}$; 1164.7 $[M-3H]^{3-}$, 1172.2 $[M-3H+Na]^{3-}$; 873.3 $[M-4H]^{4-}$; 698.6 $[M-5H]^{5-}$; Calculated MW 3496.9.

SCHEME III-Part 1

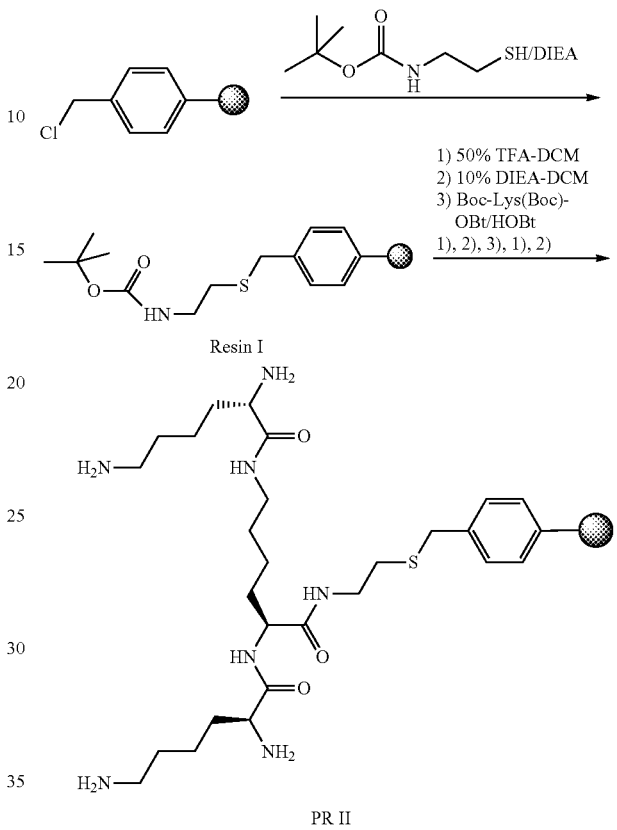

SCHEME III-Part 2A

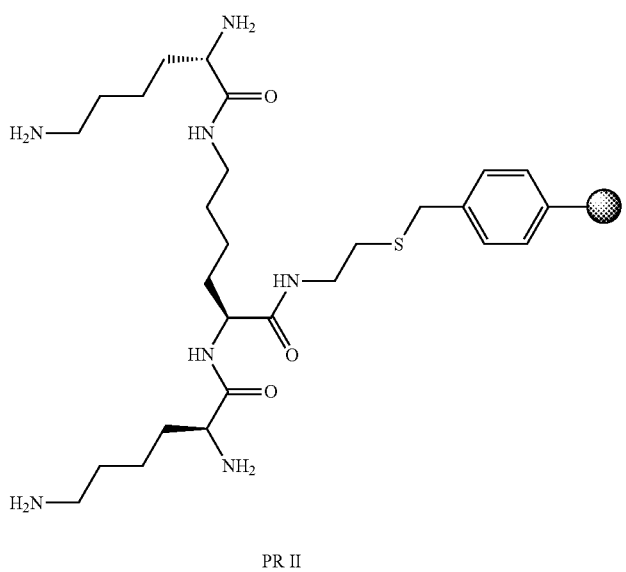

PR II

3), 1), 2)
Boc-Tyr(Bzl)-ONp/HOBt
1), 2)

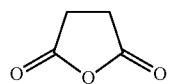

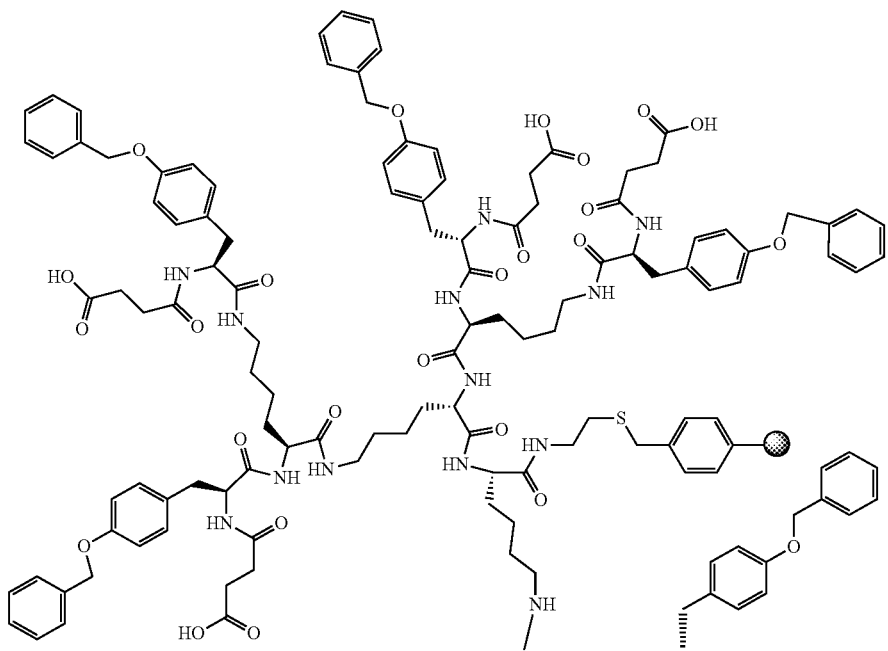
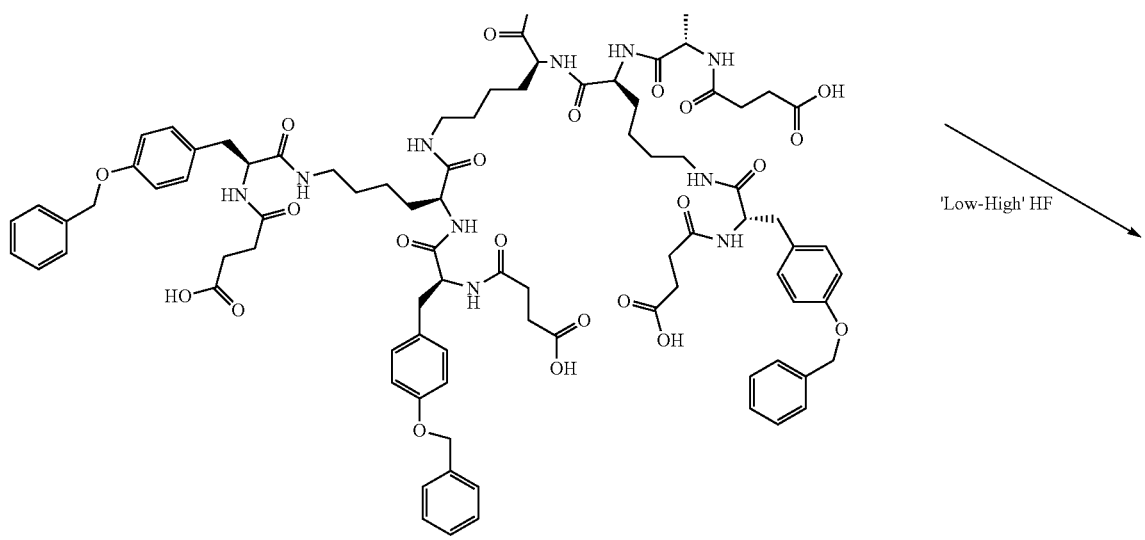
PR III

-continued
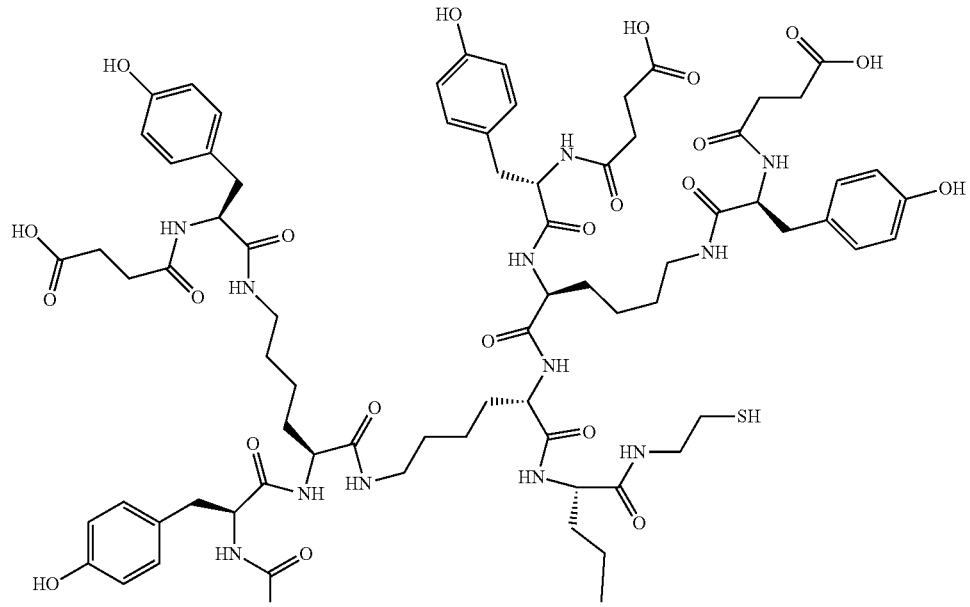
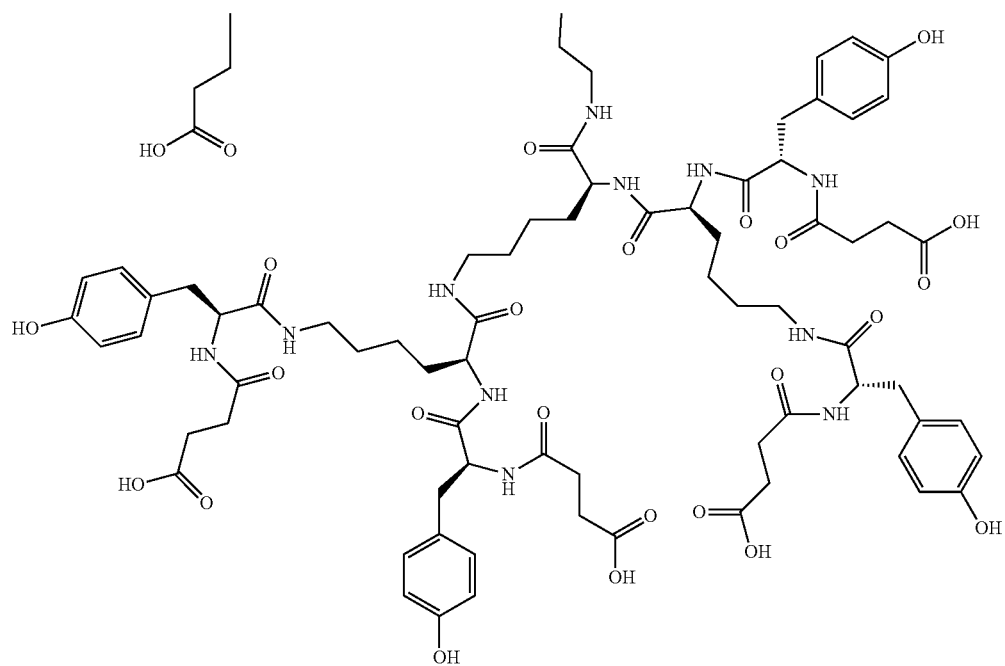
Tyr8-dendron

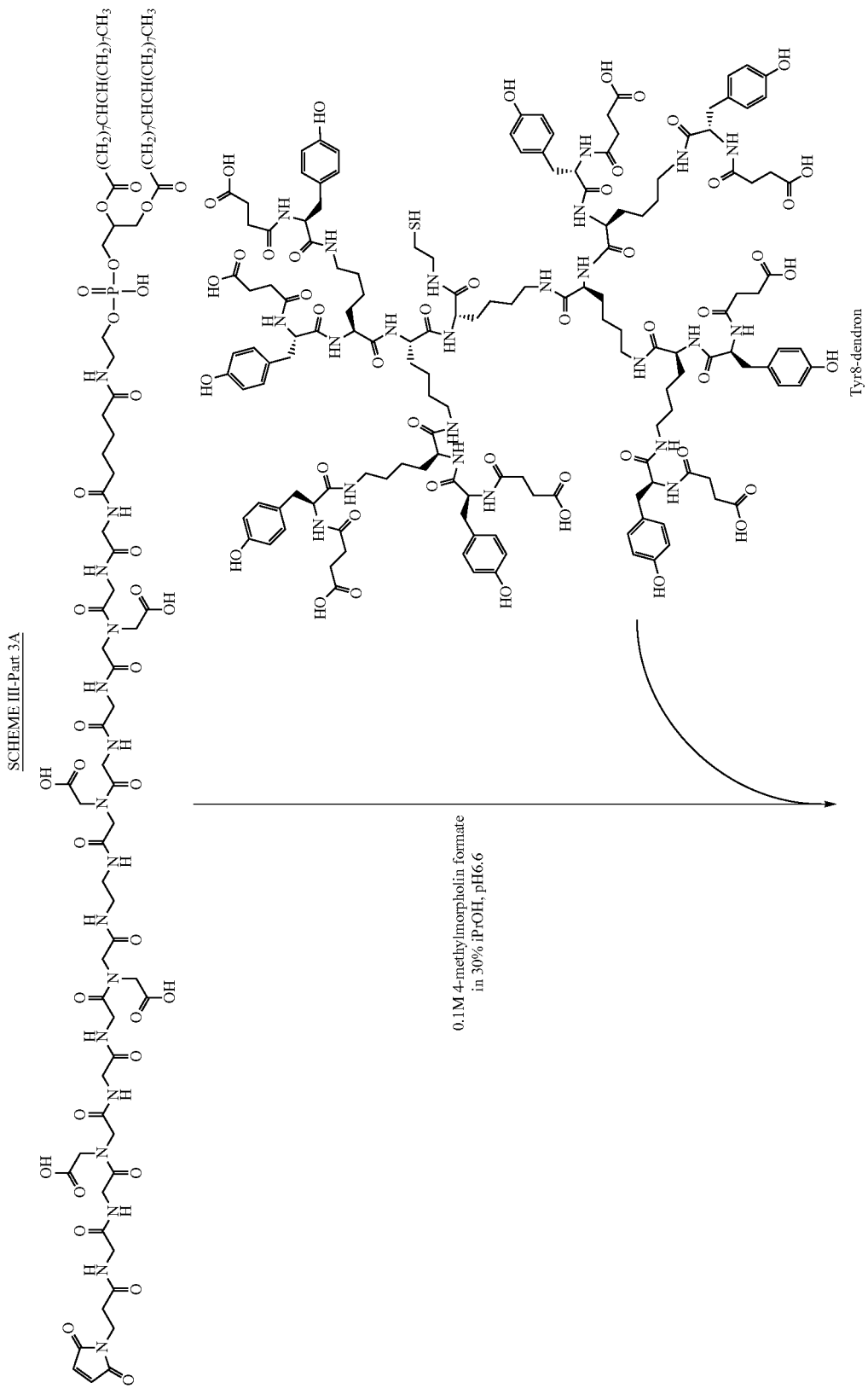

-continued
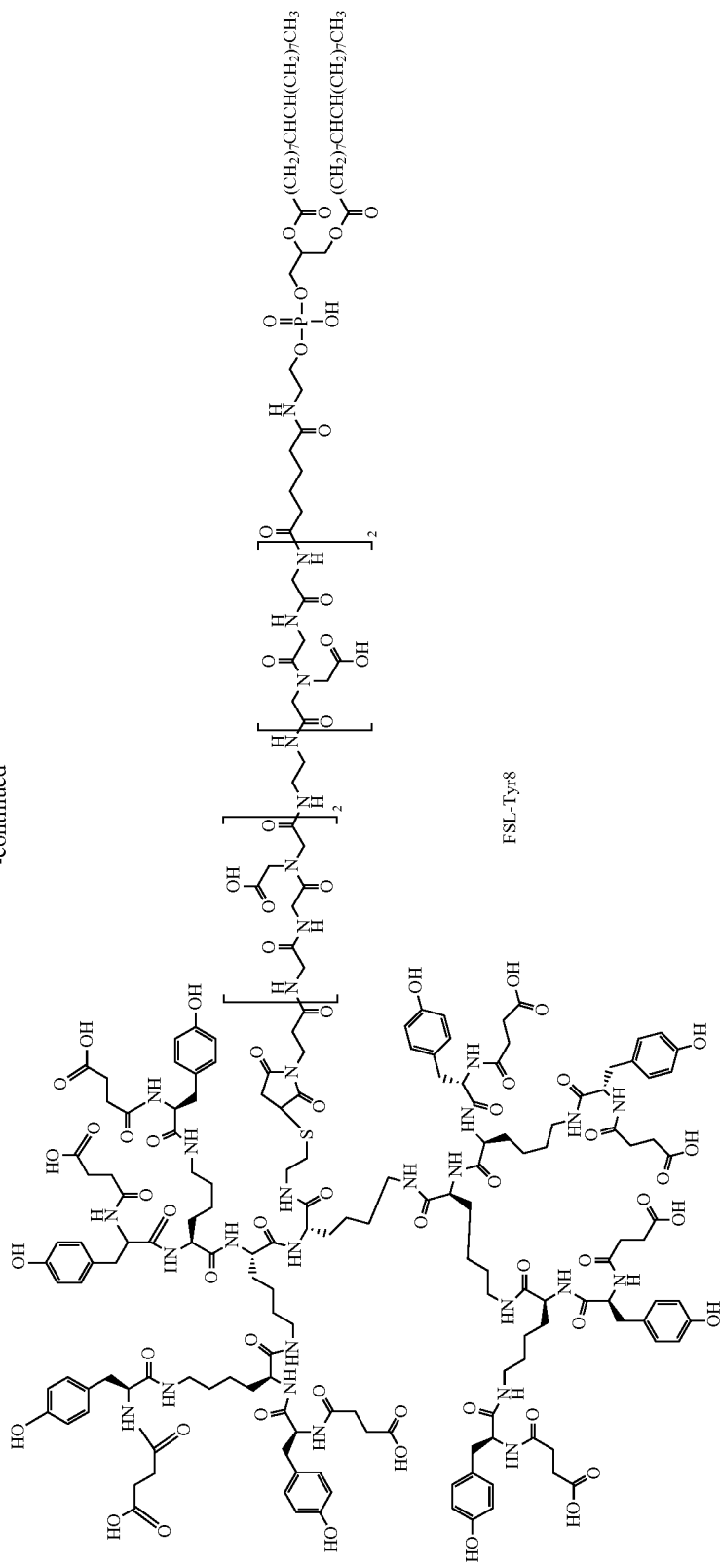
FSL-Tyr8

SCHEME III-Part 2B
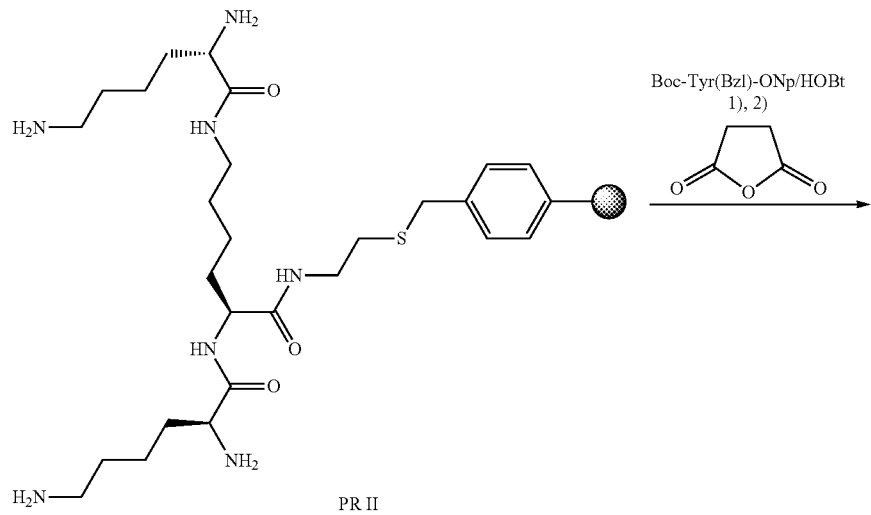
PR II
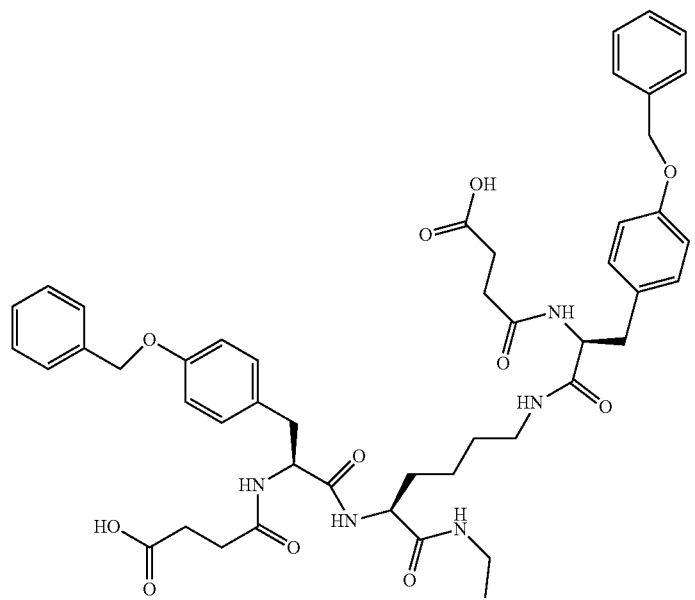

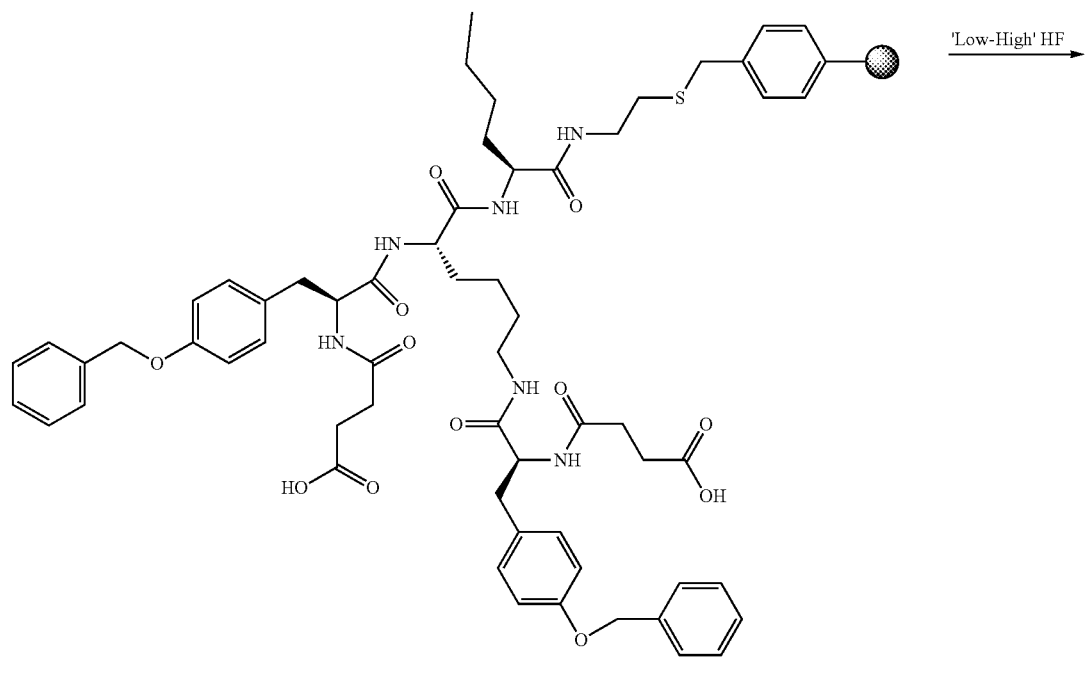
PR IV
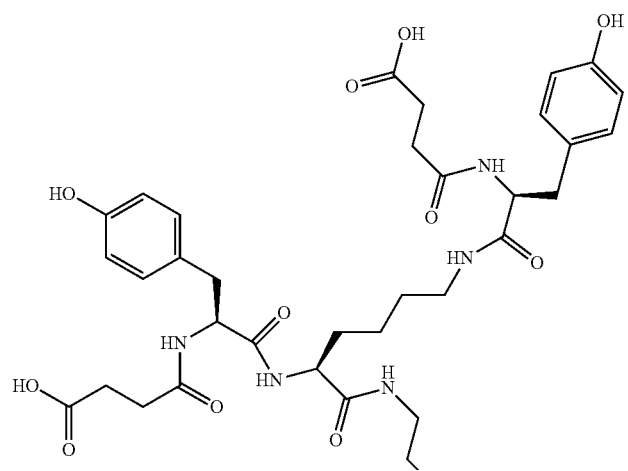

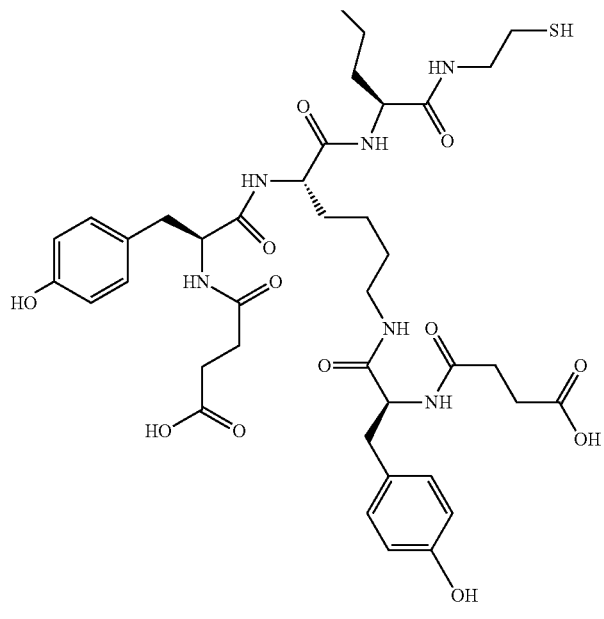
Tyr4-dendron

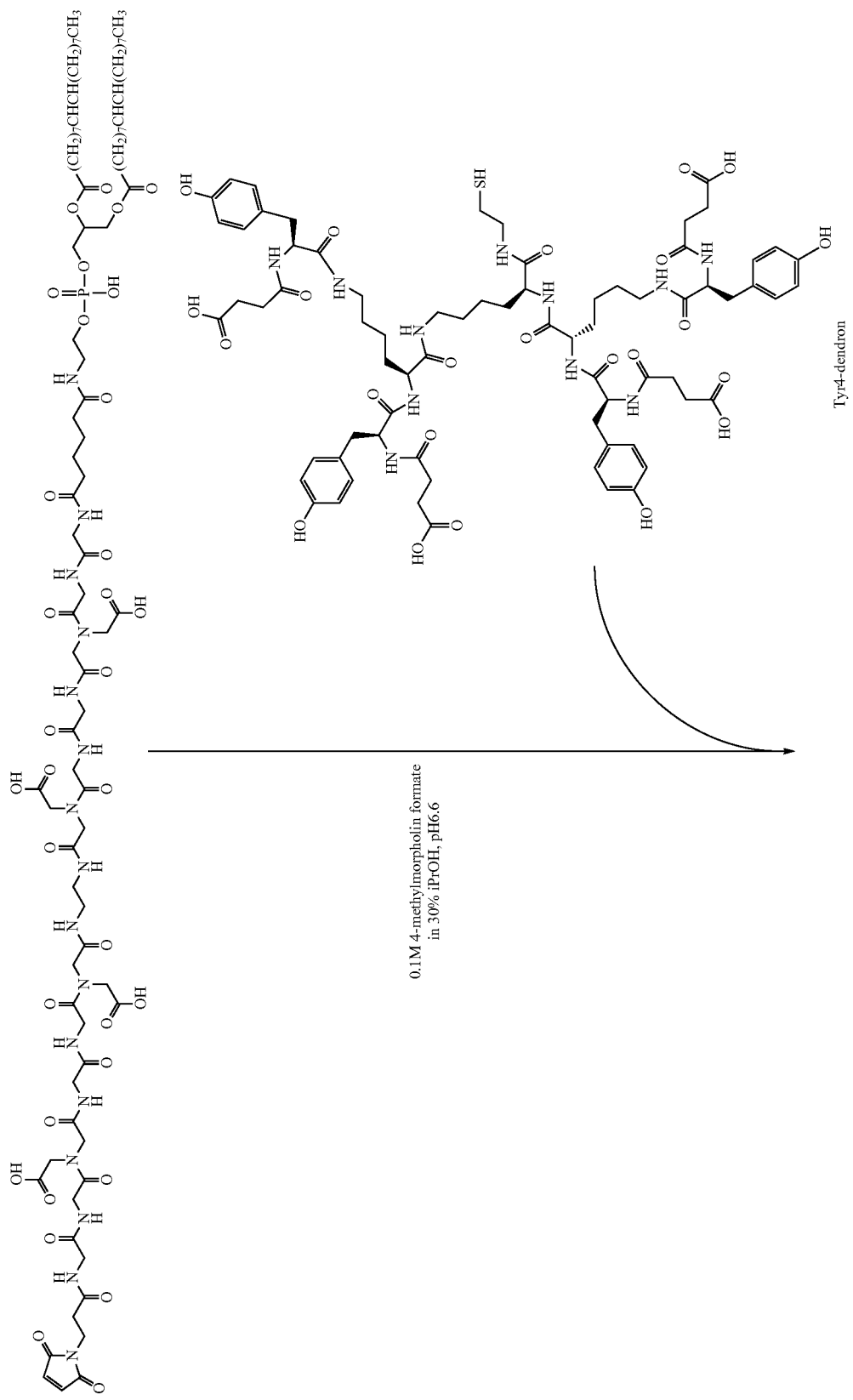

-continued
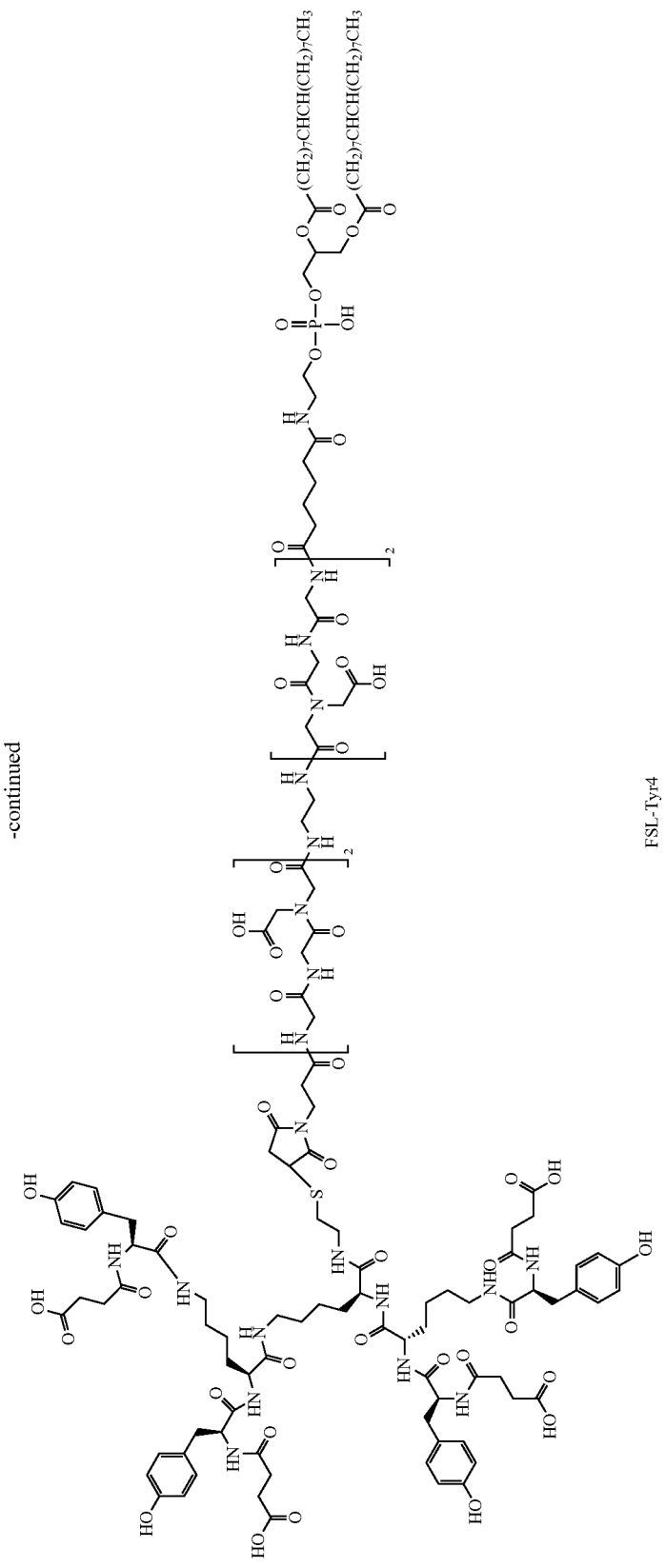
FSL-Tyr4

The following procedures and results are also described and discussed in the publication of Hadac et al (2011).

Iodination of the Construct FSL-Tyr

To oxidatively label the tyrosine residue of the construct we Pierce (Cat. 28601, Thermo Fisher Scientific Inc., Rockford, Ill.) iodination tubes were used. Briefly, a Pierce Iodination tube was wetted with 1 ml Tris-HCl—NaCl buffer (25 mM Tris-HCl pH 7.5, 0.4 M NaCl) and decantanted. In a well vented fume hood, 100 μl Tris-HCl—NaCl buffer followed by 1 mCi Na$^{125}$I (Cat. NEZ-033A Perkin-Elmer, Cambridge, Mass.) was added and incubated at room temperature for 6 minutes swirling every 30 seconds. The activated Na$^{125}$I was transferred to a new tube containing the construct designated FSL-tyrosine (0.3 mg/150 μL) and incubated at room temperature for 8 minutes, swirling every 30 seconds. The solution was then transferred into the sample reservoir of a Microcon-10 filter device (Millipore Corporation, Billerica, Mass.) and 250 μL Tris-HCl—NaCl buffer added to the reservoir, sealed and spun in a microcentrifuge in a fume hood for 30 minutes at 13,000 rpm. The flow through (FT1) was collected and 300 μl Tris-HCl—NaCl buffer added to the sample reservoir. The centrifugation was repeated with collection of the flow through (FT2) and retained sample (iodinated($^{125}$I) FSL-tyrosine). All fractions were quantified in a dose calibrator and aliquots of the iodinated ($^{125}$I) FSL-tyrosine stored at −20° C.

Modification of VSV with the Construct Designated FSL-Fluorescein

A volume of 1.25 μL of FSL-fluorescein (20 or 200 μg/ml) to provide a final concentration of 1 and 10 μg/ml was added to 25 μL of VSV ($7.8\times10^{10}$ $TCID_{50}$ units/mL). The suspension of VSV and FSL-fluorescein were incubated for 2 hours at 37° C. Sample of VSV modified to incorporate the construct (VSV-FSL-FLRO4) and control samples of virus were then fixed with 4% paraformaldehyde on ice for 10 minutes.

Modification of H1N1 with the Construct Designated FSL-Fluorescein 0.5 mg of FSL-fluorescein was dispersed in 50 μL 50 mM $NaHCO_3$, pH 8.3 followed by addition of 450 μL 0.1M PBS. The obtained stock solution was used for preparation of three concentrations; 25, 100, and 200 μg/mL. To modify virus 60 μL of the stock solution was added to an equal volume of virus preparation and incubated at room temperature for 1 h. An excess of FSL-fluorescein was removed using chromatography on Sephadex G-50. Modified virus was stored in 0.1 M PBS containing 0.01% $NaN_3$.

Influenza Virus (H1N1) Infectivity Test

Infectivity of H1N1 was tested on swine testicles cell culture (ST cells). A 24-well plate with cells was washed with 1% BSA in PBS (PBA) followed by infection with 200 μl virus preparation (200 HAU) in PBS. Cells were incubated with virus at 37° C. for 1 h followed by washing two times with PBA. The cell monolayer was treated with trypsin solution and the obtained cell suspension washed with PBA and fixed in 0.1% formaldehyde solution in PBS. Cell fluorescence was measured using a laser flow cytometer DACO Galaxy (Denmark) at 488 nm.

Modification of BV-NIS by FSL-Fluorescein and Subsequent Labelling of KAS6/1 Cells A volume of 5 μL of FSL-fluorescein (100 μg/ml) was added to 100 μL of MV-NIS ($1.5\times10^8$ $TCID_{50}$ units/mL) and incubated for 2 hours at 37° C. to prepare MV-FSL-FLRO4. The suspension was then diluted to 250 μl with PBS. KAS6/1 cells were grown in RPMI 1640 supplemented with heat-inactivated 10% fetal bovine serum, 100 U/mL penicillin, 100 mg/mL streptomycin and interleukin-6 (IL-6, 1 ng/mL). A volume of 140 μL of the MV-FSL-FLRO4 preparation was added to 100 μL of a KAS6/1 cell suspension ($4\times10^6$/100 μL) in OptiMEM (Invitrogen, Carlsbad Calif.) media and incubated at 37° C. for 1 hour. Following incubation the resultant MV-FSL-FLRO4 labelled KAS6/1 cells were pelleted and washed once (PBS with 1% BSA) by centrifugation and fixed on ice for 10 minutes in 4% paraformadehyde.

Modification of Vero Cells with Iodinated ($^{125}I$) FSL-Tyr

In 6-well tissue culture plates $5\times10^5$ Vero cells maintained in Dulbecco-modified Eagle medium containing 10% fetal bovine serum (American Type Culture Collection, Manassas, Va.) per well were grown to confluence overnight then washed with HBSS 10 mM HEPES pH 7.3 with KOH. A volume of 1 mL of HBSS-HEPES (10 mM HEPES, pH 7.3) was added to a monolayer followed by varying amounts of the iodinated construct or $^{125}I$ to give 1, 2 or $4\times10^7$ cpm per well. After a 2-hour incubation at 37° C. the plate was placed on ice, the supernatant aspirated, and the monolayer washed with 1 ml of iced HBSS buffer. Cells were lysed with 1 ml of 1M NaOH and each lysate transferred to a test tube for quantitation of radioactivity.

Monitoring Distribution In Vivo

To determine the distribution of labelled virus in mice 200 μl of VSV-hIFNβ ($5.8\times10^{10}$) was added to 150 μCi of iodinated ($^{125}I$) FSL-tyrosine and incubated for 4 hours at room temperature. Syringes were then loaded each with a total of 50 μCi of labelled virus (VSV-FSL-$^{125}I$). Control syringes were also loaded each with 50 μCi, two with $Na^{125}I$ and two with iodinated ($^{125}I$) FSL-tyrosine (FSL-$^{125}I$). Each of seven mice were injected IP with one of the $^{125}I$ reagents. Prior to imaging mice were anesthetized with inhalation of isoflurane and imaged 1 hour post sample injection using micro-SPECT/CT system (X-SPECT, Gamma Medica Ideas) and image analysis using PMOD software (PMOD Biomedical Image Quantification and Kinetic Modeling Software, PMOD Technologies Zurich, Switzerland). One mouse from each sample group underwent additional imaging at 4 and 24 hour time-points. After each final imaging point the mouse was sacrificed, dissected and radioactivity in organs was quantified in a dose calibrator.

FACScan Flow Cytometry

Samples were analyzed by FACScan flow cytometry and Cell Quest Pro software (BD Biosciences, San Jose, Calif.).

Quantitation of Radioactivity

Radioactivity was quantitated with an Isodata-10 gamma spectrometer (Polymedio, Yorktown Heights, N.Y.) and radioisotope calibrator (model CRC-5R, Capintec, Inc. Ramsey, N.J.).

Results

The iodinated ($^{125}I$) form of the construct designated FSL-tyrosine (FSL-$^{125}I$) had the spontaneous and controlled membrane insertion character of other FSL constructs. Its ability to label Vero cells has been investigated and contrasted with direct $^{125}I$ labelling. It has been shown that at equivalent radioactive counts, FSL-$^{125}I$ was about 10-fold more effective at labelling cells than $^{125}I$ and the labelling occurred in a concentration dependent manner (FIG. 5). A comparison of $^{125}I$ and FSL-$^{125}I$ labelling of MV and VSV, and subsequent sucrose gradient purification showed that more FSL-$^{125}I$ labelled virions than $^{125}I$ labelled virions, could be isolated in the sucrose fraction, compared with the buffer, where the unbound label is predominantly found (FIG. 6).

VSV was determined to be labelled with FSL-FLRO4 in a manner similar to cells (Blake et al (2010)) by contacting VSV with the FSL-FLRO4 to create modified virus (VSV-

Figure 8:
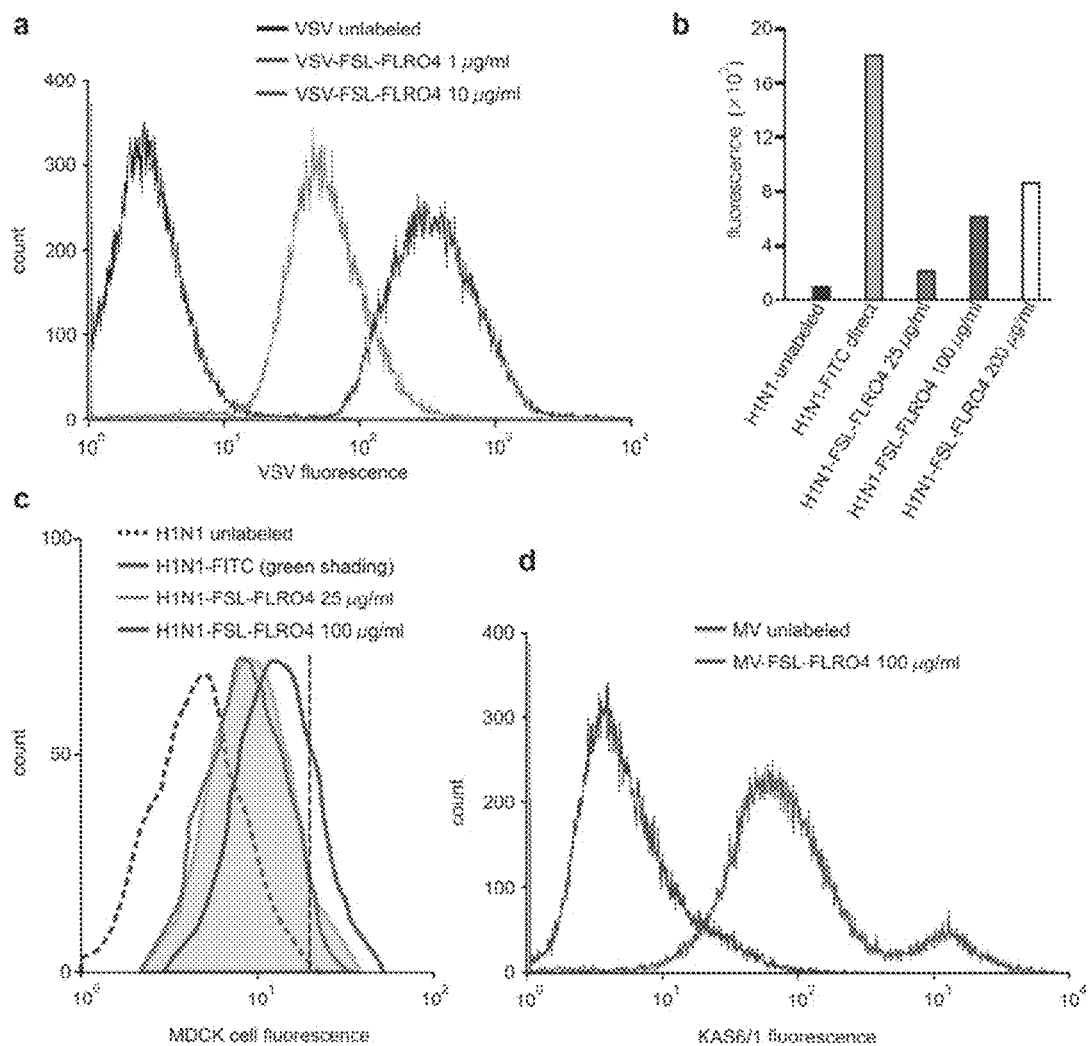
FIG. 8. FSL-fluorescein (FSL-FLRO4) labelling of virions. (a) FACScan of FSL-fluorescein modified VSV. (b) Total fluorescence of H1N1 samples (8 haemagglutinin units of virus was taken in all cases) and labelled directly with FITC or modified with different concentrations of FSL-fluorescein (FSL-FLRO4). The fluorescence was read in 96-well plate with infectivity of the virions or their ability to bind cell membranes as demonstrated by H1N1 fusion with ST cells and MV binding to KAS6/1 cells.

FSL-FLRO4) and analysing by FACScan (FIG. 8(a)). By simply increasing the concentration of FSL construct, the intensity of modified virions increased (FIG. 8(a)). Similarly, H1N1 modified with FSL-FLRO4 showed a concentration dependent modification (FIG. 8(b)). For comparison H1N1 was labelled by the conventional direct FITC method (Yoshimura and Ohnishi (1984)) which gave about 9-times greater total fluorescence than H1N1 modified with 25 µg/ml FSL-FLRO4 (FIG. 8(b)). However, when these labelled and modified H1N1 virions were allowed to infect ST cells, essentially the same level of fluorescence was seen for 25 µg/ml FSL-FLRO4 modified as with direct FITC-labeled H1N1 (FIG. 8(c)). This result, starting with the 9-times more fluorescence of direct FITC labelled H1N1 yet obtaining only equivalent fluorescence with the 25 µg/ml FSL-FLRO4 modified H1N1 post infection of MDCK cells, can be interpreted to mean that 9-times less FITC labelled virions infected the MDCK cells. Thus, the FSL-FLRO4 labelled virions appears to conserve infective potency better than FITC-labelled virions, perhaps, due to the non-covalent nature of the modification. When a higher concentration FSL-FLRO4 construct modified H1N1 was used to infect MDCK cells (e.g. 100 and 200 µg/ml) increased fluorescent intensity was obtained (FIG. 8(b)).

MV was modified with FSL-FLRO4 (MV-FSL-FLRO4) and then allowed to react with a KAS6/1 cell line suspension (FIG. 8(d)). These results, like those for H1N1 (FIG. 8(c)) show that the modified viruses retain their ability to bind to cells, and become detectable by flow cytometry. The additional small peak seen with KAS6/1-MV-FSL-FLRO4 cells (FIG. 8(d)) is probably due to dead cells, as unbound virus was excluded by gating.

Figure 9:
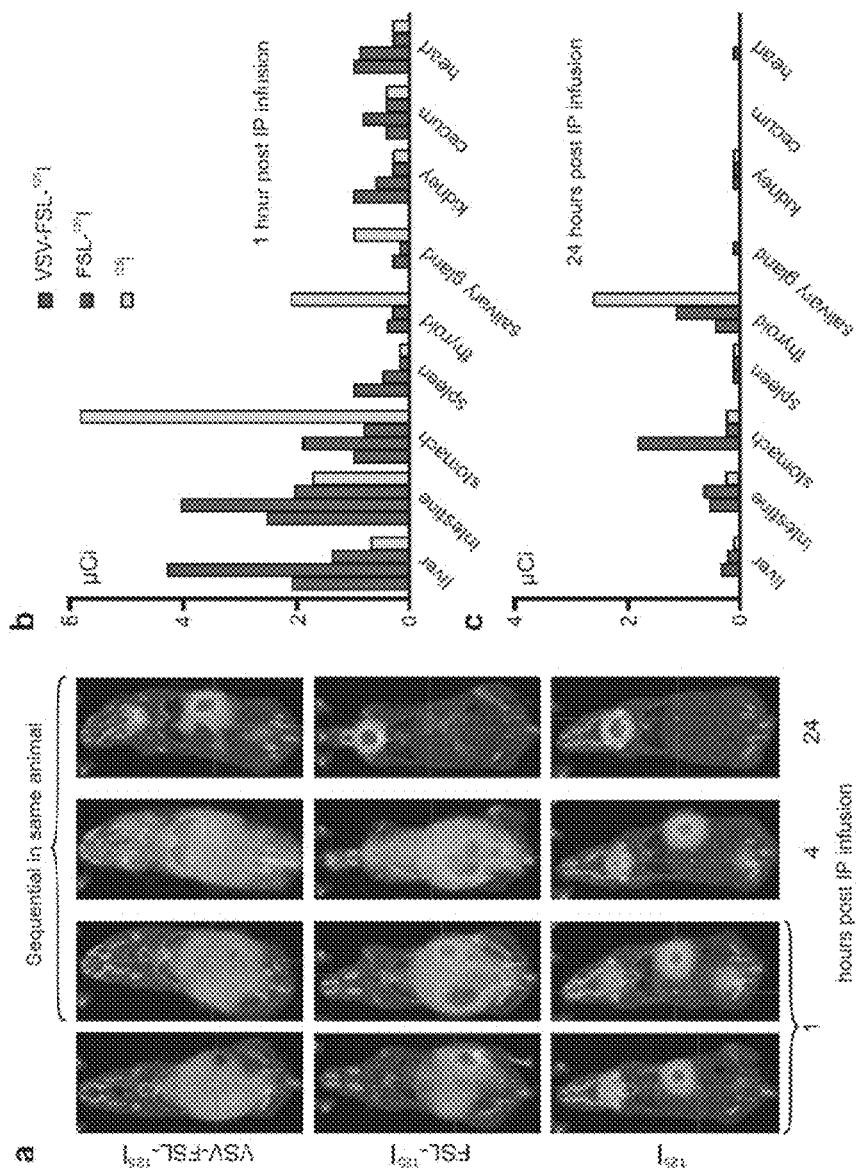

Following peritoneal infusion we compared the distribution in vivo of $^{125}$I and FSL-$^{125}$I construct with that of VSV-FSL-$^{125}$I (FIG. 9). Radioactive iodine has a very well described distribution in vivo (Hammond et al (2007)) to thyroid, salivary glands, stomach and bladder and the $^{125}$I results were concordant with the literature. Within 1 hour post administration to the peritoneal cavity labelled virions (VSV-FSL-$^{125}$I), in contrast to $^{125}$I and FSL-$^{125}$I, localized to liver, spleen and bloodstream—with some signal also retained in the peritoneal cavity (FIGS. 9(a) and 9(b)). Intravenously administered VSV-FSL-$^{125}$I localized similarly, but without the strong peritoneal signal (not shown). FSL-$^{125}$I alone followed a similar distribution to labelled virus, but was significantly different to free $^{125}$I, which rapidly distributed to the stomach and then to the thyroid (FIG. 9(a)). Due to the variable nature of urine collection bladder quantitation was not considered. At 4-hours post infusion the distribution (FIG. 9(a)) had not changed significantly from the 1 hour time point although more systemic spread had occurred. At 24 hours (FIGS. 9(a) and 9(c)) both $^{125}$I and FSL-$^{125}$I injected animals gave essentially only thyroid distribution while the VSV-FSL-$^{125}$I injected animals had a distribution equivalent to the 1 hour distribution of $^{125}$I. The accumulation of radioactive iodine in the thyroid from both VSV-FSL-$^{125}$I and FSL-$^{125}$I is not surprising and suggests that degradation of the FSL-$^{125}$I had occurred releasing free iodide, which then was concentrated in the thyroid gland.

Although the invention has been described with reference to embodiments or examples it should be appreciated that variations and modifications may be made to these embodiments or examples without departing from the scope of the invention. Where known equivalents exist to specific features, such equivalents are incorporated as if specifically referred to in this specification. In particular the substitution of the less favoured particle emitting radioisotope $^{131}$I for $^{125}$I in any of the claimed methods is recognised to be within the scope of the invention.

REFERENCES

Barr et al (2010) *Function-Spacer-Lipid (FSL) constructs enable inkjet printing of blood group antigens* FEBS J, Vol 277 (S1), 235.

Blake et al (2003) Embryo modification and implantation international application no. PCT/NZ03/00059 (publ. no. WO 03/087346).

Blake et al (2010) *Fluorophore-kodecytes-fluorescent function-spacer-lipid (FSL) modified cells for in vitro and in vivo analyses* FEES J, Vol 277 (S1), 199.

Bovin et al (2009) Functional lipid constructs international application no. PCT/NZ2008/000266 (publ. no. WO 2009/048343).

Campos et al (2004) *Avidin-based targeting and purification of a protein IX-modified, metabolically biotinylated adenoviral vector* Mol Ther, Vol 9, 942-954.

Chesla et al (2010) *Solid phase syphilis test utilizing KODE technology* Transfusion, Vol 50 (S1), 196A-197A.

Frame et al (2007) *Synthetic glycolipid modification of red blood cell membranes* Transfusion, Vol 47, 876-882.

Hadac et al (2011) *Fluorescein and radiolabelled function-spacer-lipid constructs allow for simple in vitro and in vivo bioimaging of enveloped virions* J. Virological Methods, 176, 78-84.

Hammond et al (2007) *A gama camera re-evaluation of potassium iodide blocking efficiency in mice* Health Phys, Vol. 92, 396-406.

Harrison et al (2010) *A synthetic globotriaosylceramide analogue inhibits HIV-1 infection in vitro by two mechanisms* Glycobiology, Vol 27, 515-524.

Heathcote et al (2010) *Novel antibody screening cells, MUT+Mur kodecytes, created by attaching peptides onto erythrocytes* Transfusion, Vol 50, 635-641.

Henry (2009) *Modification of red blood cells for laboratory quality control use* Curr Opin Hematol, Vol 16, 467-472.

Hermanson (2008) *Bioconjugation Techniques*, $2^{nd}$ ed., Academic Press.

Herschman (2003) *Molecular imaging: Looking at problems, seeing solutions* Science, Vol 302, 605-608.

Kaiser et al (1970) Anal. Biochem., 34(2), 595-8.

Korchagina et al (2008) Fluorescent cell markers international PCT application no. PCT/NZ2007/000256 (publ. no. WO 2008/030115).

Kuruppu and Tanabe (2005) *Viral oncolysis by herpes simplex virus and other viruses* Cancer Biol Ther, Vol 4, 524-531.

Lui et al (2007) *Clinical trial results with oncolytic virotherapy: a century of promise, a decade of progress* Nat Rev Clin Oncol, Vol 4, 101-117.

Oliver et al (2011) *Modeling transfusion reactions and predicting in vivo cell survival with kodecytes* Transfusion; (in press).

Peng et al (2003) Hum Gene Ther, Vol, 14, 1565-1577.

Piwnica-Worms et al (2004) *Molecular imaging of host-pathogen interactions in intact small animals* Cell Microbiol, Vol 6, 319-331.

Räty et al (2006) *Magnetic resonance imaging of viral particle biodistribution in vivo* Gene Ther, Vol 13, 1440-1446.

Stokke et al (1974) *Lipid composition and cholesterol esterification in lymph* Scand J Clin Lab Invest, Vol 33, 199-206.

Strable and Finn (2009) *Chemical modification of viruses and virus-like particles* Curr Top Microbiol Immunol, Vol 327, 1-21.

Tam (1985) *A gradative deprotection strategy for the solid phase synthesis of peptide amides using p-(acyloxy)benzhydrylamine resin and the SN2 deprotection method* J. Org. Chem., 50, 5291-5298.

Tam and Merrifield (1987) *Strong acid deprotection of the synthetic peptides: mechanisms and methods* Udenfriend, S., Meienhofer, J., (Eds), The Peptides: Analysis, Synthesis, Biology, Vol. 9, Academic Press, New York, pp 185-248.

Waehler et al (2007) *Engineering targeted viral vectors for gene therapy* Nat Rev Genet, Vol 8, 573-587.

Yamamoto and Curiel (2010) *Current issues and future directions of oncolytic adenoviruses* Mol Ther, Vol 18, 243-250.

Yoshimura and Ohnishi (1984) *Uncoating of influenza virus in endosomes* J Virol, Vol 51, 497-504.

The invention claimed is:

1. A non-invasive method of monitoring by radioactivity bioscanning the distribution of a biological entity in a subject in vivo comprising the steps of administering to the subject a radioiodinated form of the biological entity and imaging the subject to monitor the distribution of the radioiodinated form in the subject in vivo, where the radioiodinated form is prepared by contacting an aqueous suspension of the biological entity with a radioiodinated construct of the structure:

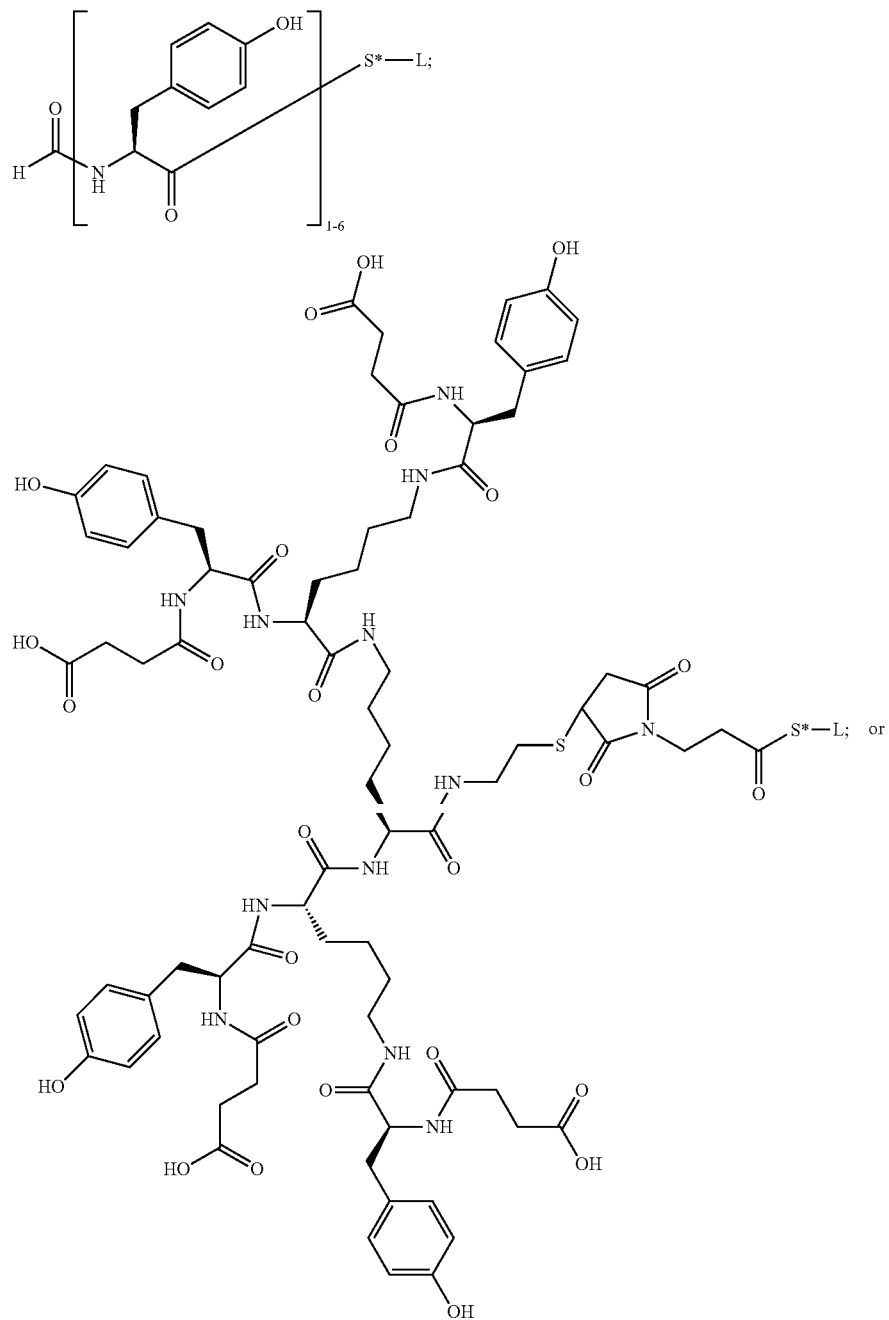

-continued
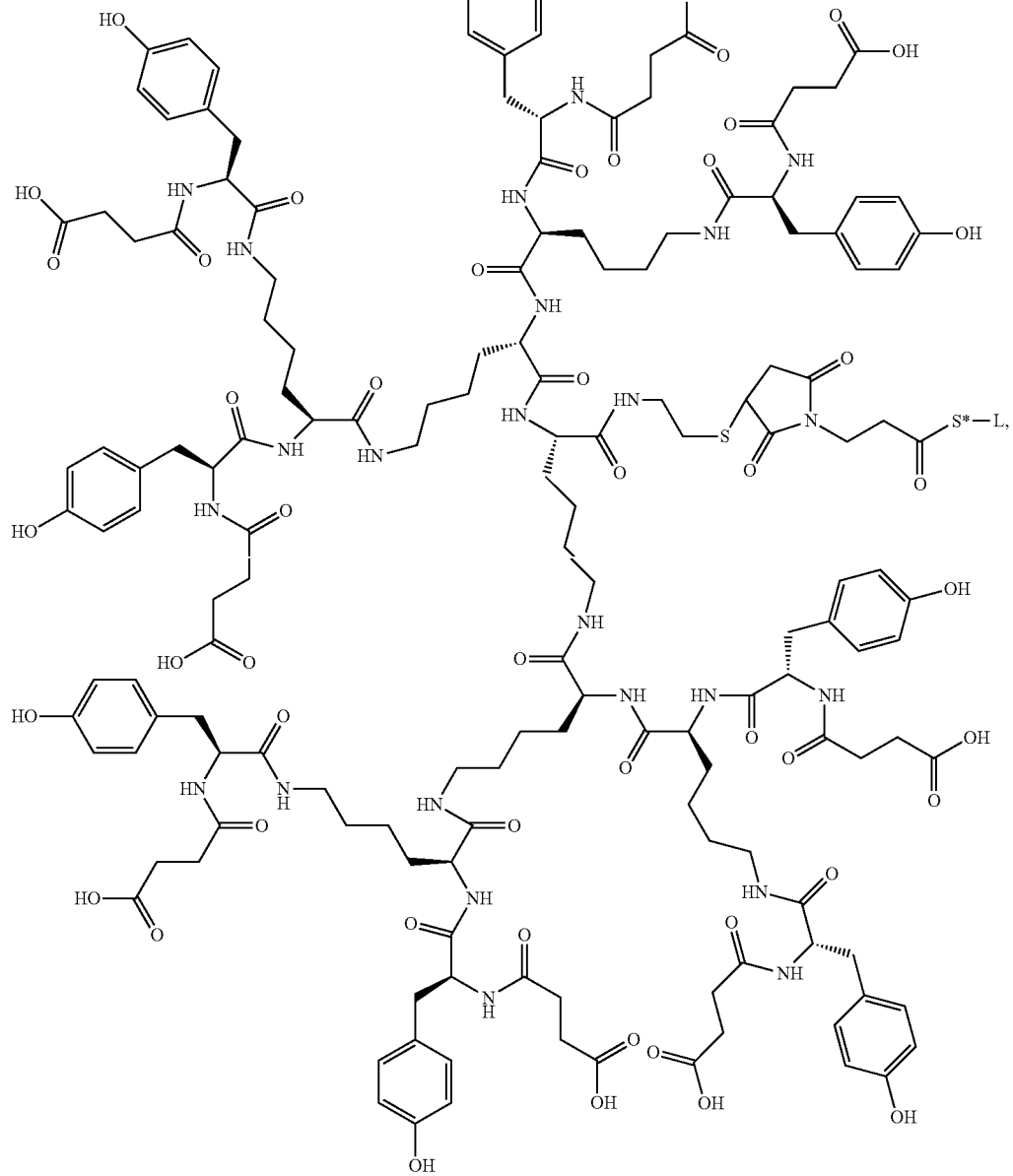
where at least one of the tyrosine residues has been radioiodinated, S* is a spacer selected to provide a construct that is readily dispersible in water, and L is a phosphatidylethanolamine.
2. The method of claim 1 where the radioiodinated construct is of the structure:
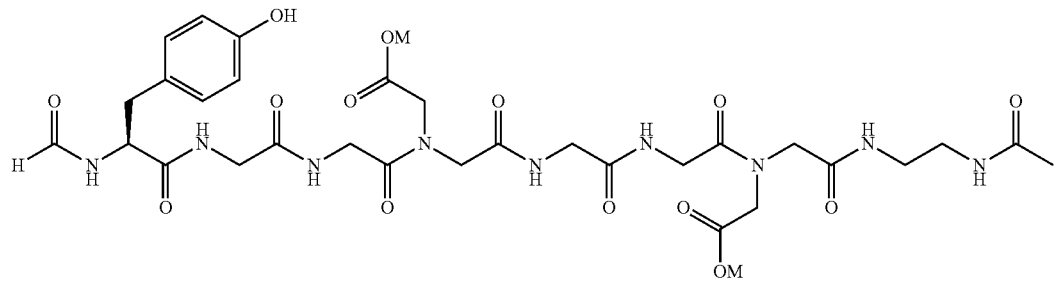

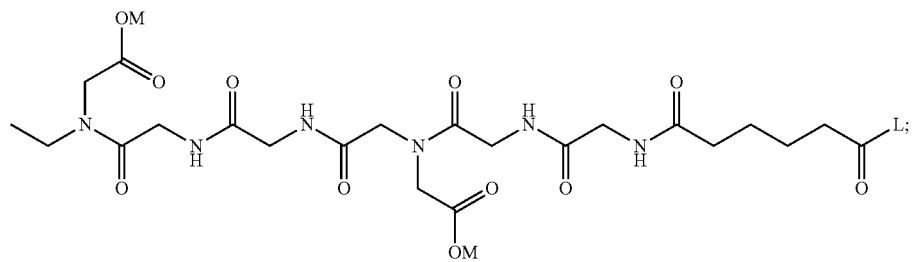
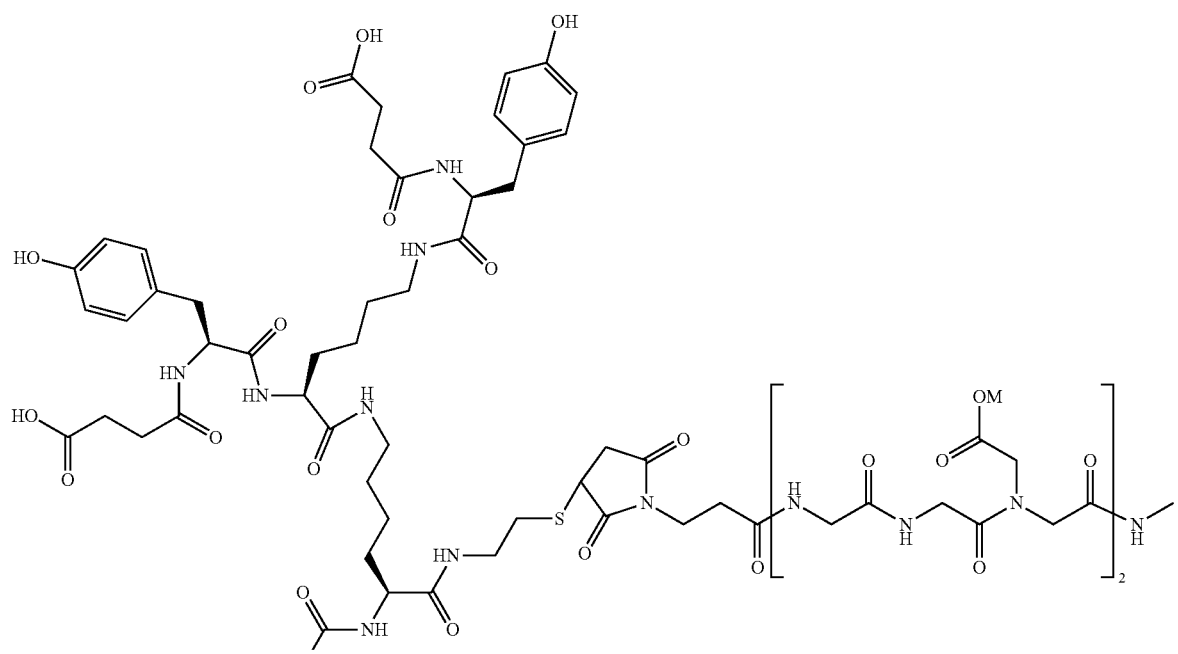
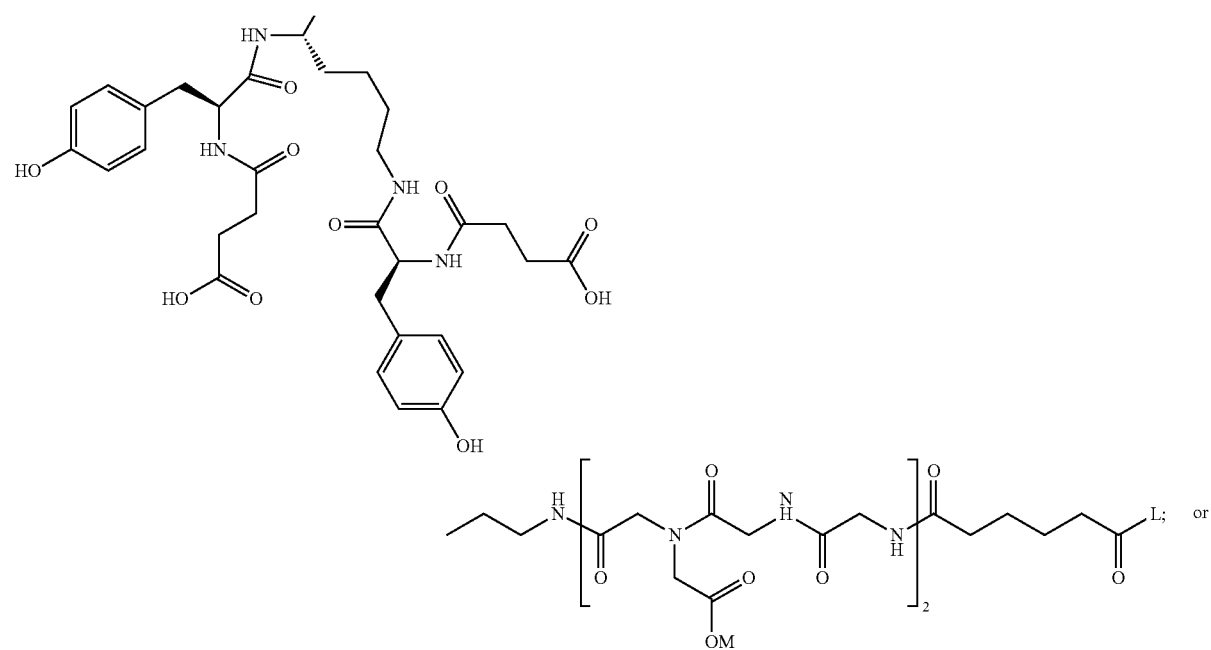

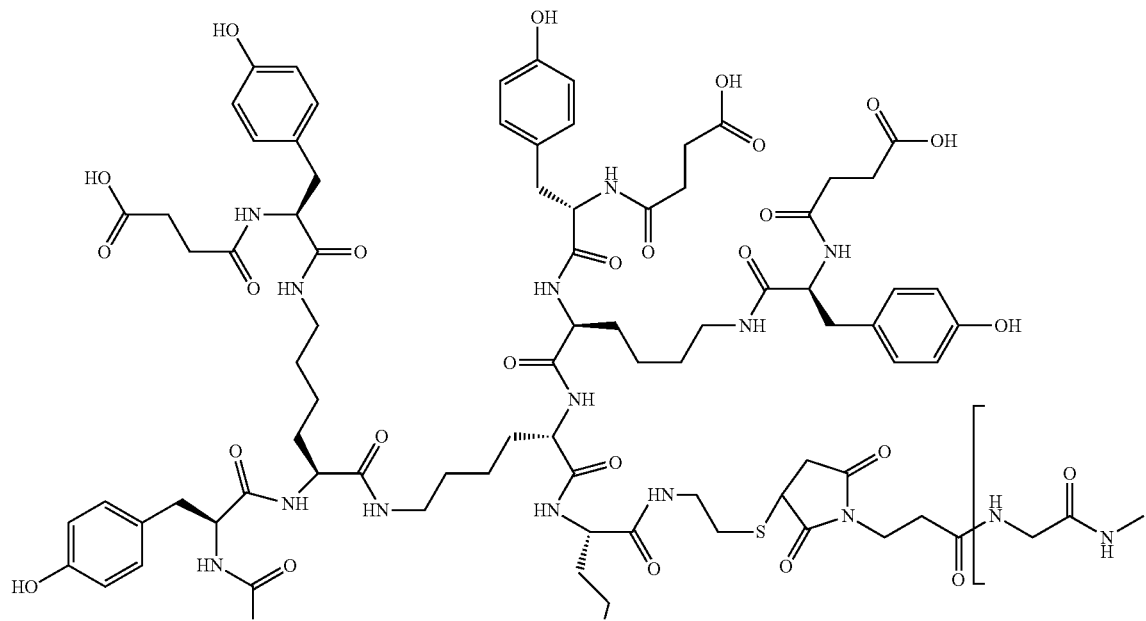
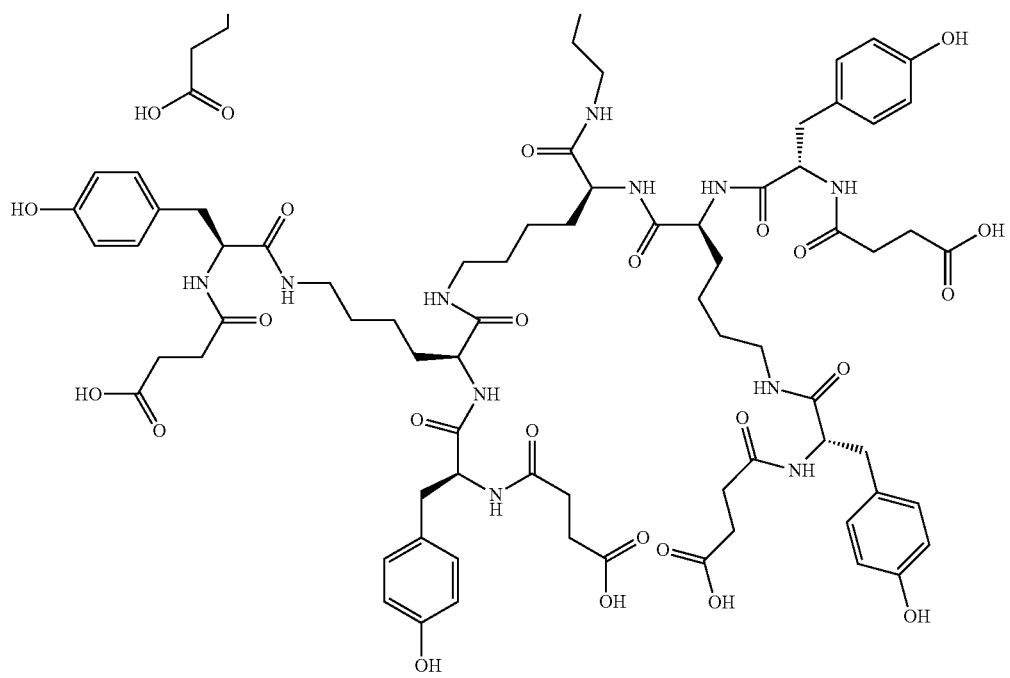

-continued

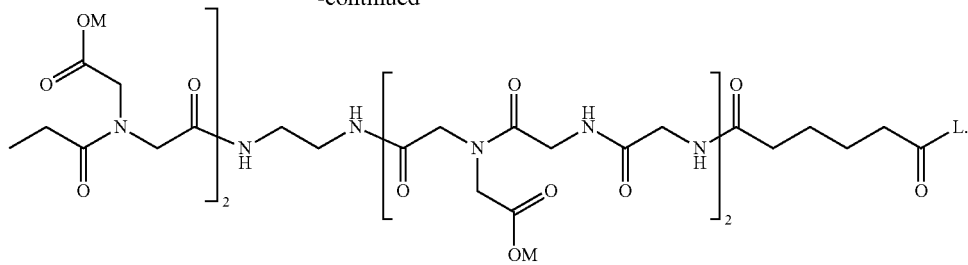

3. The method of claim 2 where the biological entity is a cell or an enveloped virus.

4. The method of claim 3 where the radioiodinated form of the biological entity is administered to the subject by injection.

5. The method of claim 4 where L is 1,2-O-dioleoyl-sn-glycero-3-phosphatidylethanolamine (DOPE).

6. The method of claim 5 where the radioiodinated construct is of the structure:

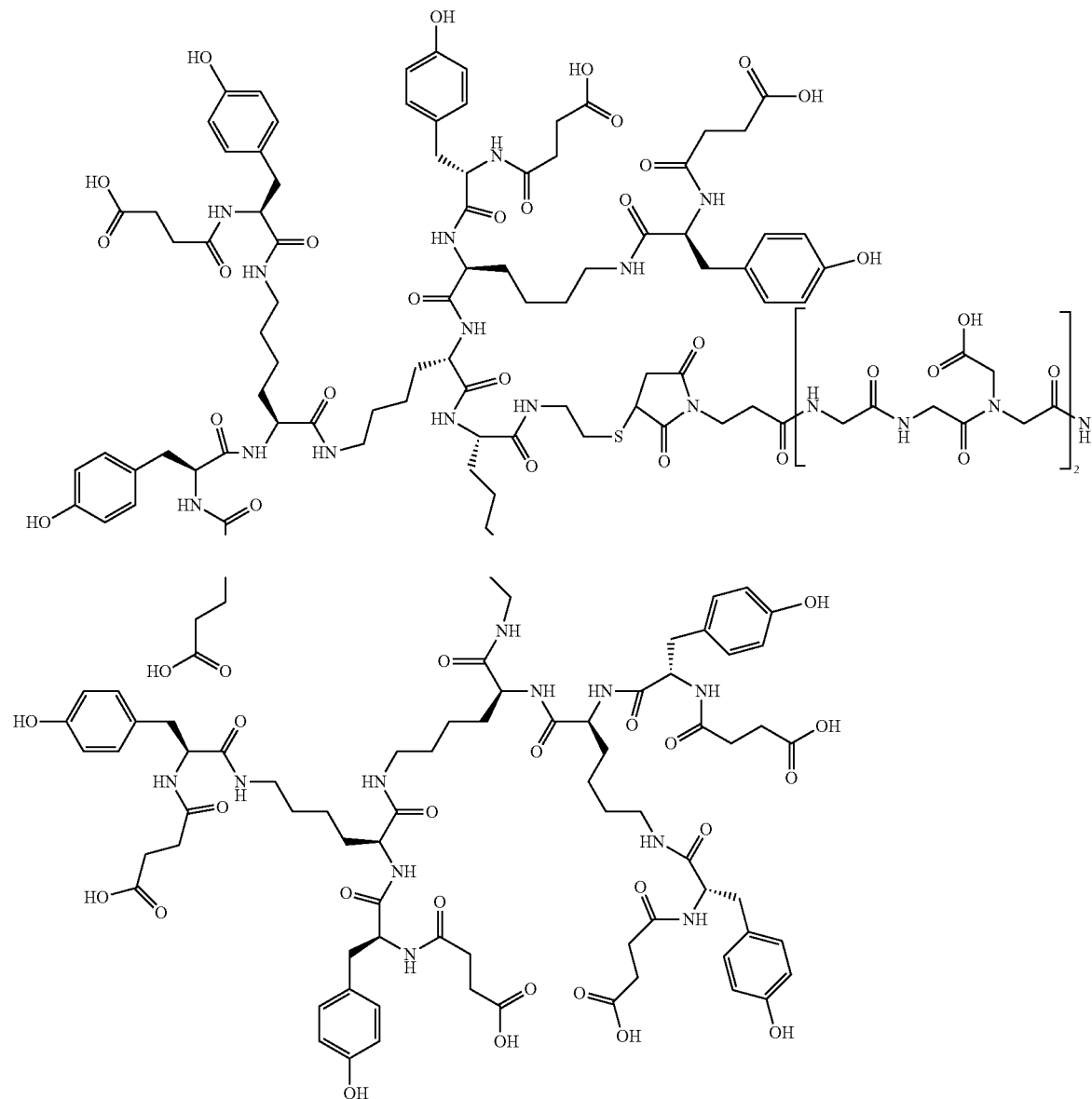

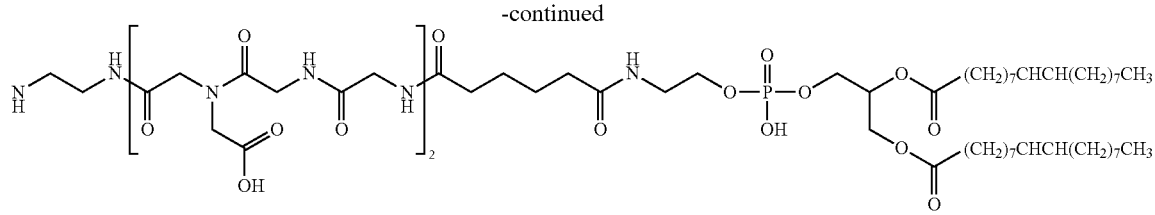
designated FSL-Tyr8.
7. The method of claim 5 where the radioiodinated construct is of the structure:
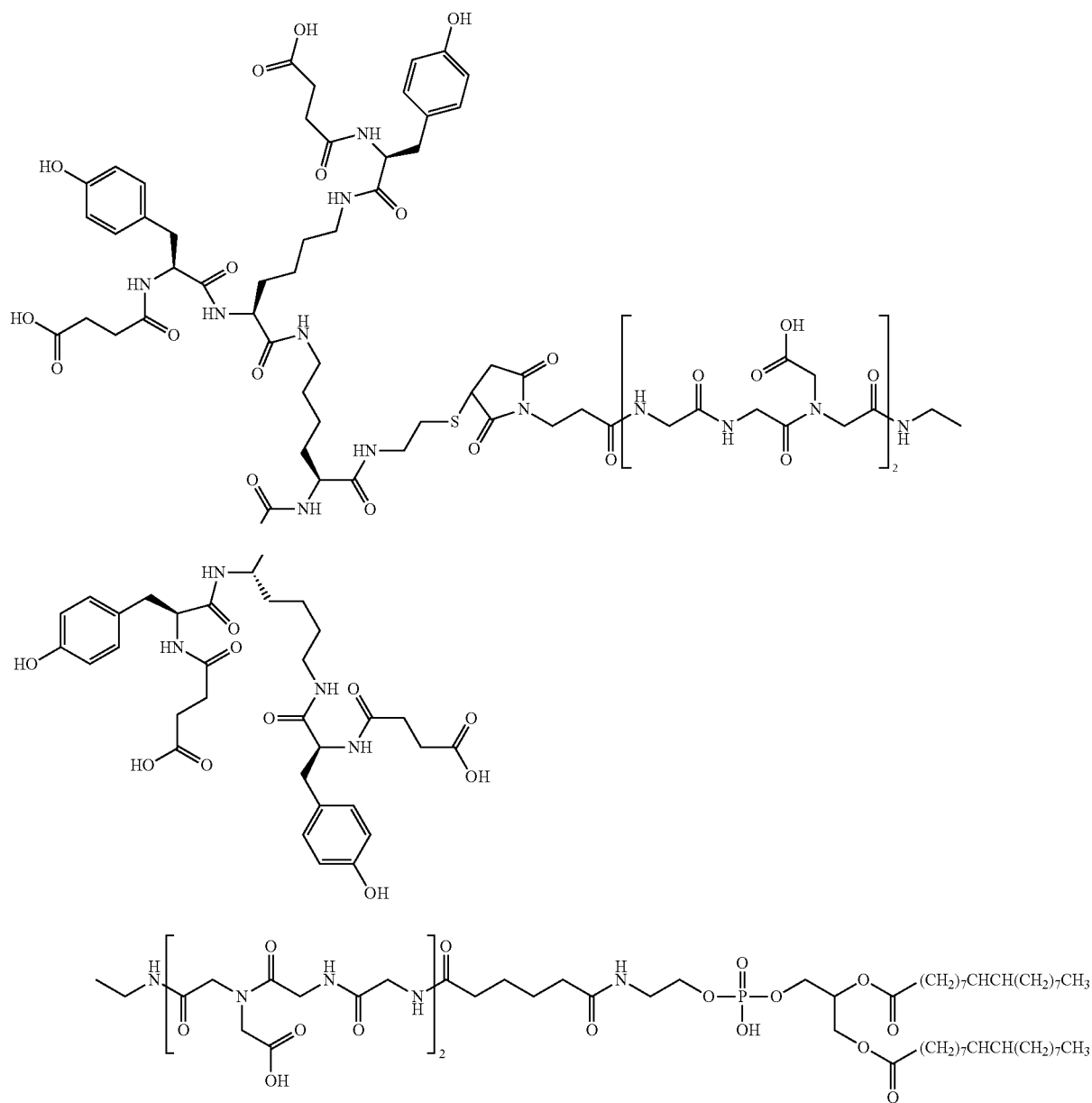
designated FSL-Tyr4.

8. The method of claim 5, where the radioiodinated construct is of the structure:
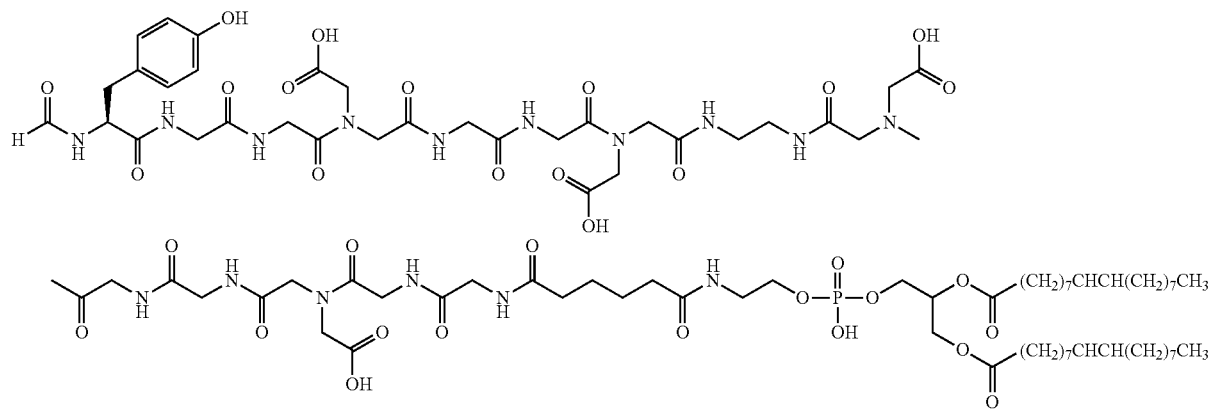
designated FSL-tyrosine.
* * * * *